US011058428B2

(12) United States Patent
Fox et al.

(10) Patent No.: US 11,058,428 B2
(45) Date of Patent: Jul. 13, 2021

(54) CIRCULAR STAPLING INSTRUMENT WITH ASYMMETRIC MOLDED SHROUD COMPONENTS

(71) Applicant: ETHICON LLC, Guaynabo, PR (US)

(72) Inventors: William D. Fox, New Richmond, OH (US); Gregory J. Bakos, Mason, OH (US); Jonathan T. Batross, Cincinnati, OH (US); John V. Hunt, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 394 days.

(21) Appl. No.: 15/717,317

(22) Filed: Sep. 27, 2017

(65) Prior Publication Data
US 2019/0090876 A1    Mar. 28, 2019

(51) Int. Cl.
*A61B 17/115*      (2006.01)
*A61B 17/11*      (2006.01)
(Continued)

(52) U.S. Cl.
CPC ....... *A61B 17/1155* (2013.01); *A61B 17/1114* (2013.01); *A61B 2017/00367* (2013.01);
(Continued)

(58) Field of Classification Search
CPC ............ A61B 17/1155; A61B 17/1114; A61B 2090/0811; A61B 2017/00367; A61B 2017/00477; A61B 2017/07221
(Continued)

(56) References Cited

U.S. PATENT DOCUMENTS 4,207,898 A * 6/1980 Becht .................. A61B 17/115
227/179.1
4,289,133 A * 9/1981 Rothfuss ............. A61B 17/115
227/175.3
(Continued)

FOREIGN PATENT DOCUMENTS

EP          2392267 A2    12/2011
WO    WO 2014/139327 A1    9/2014

OTHER PUBLICATIONS

Partial European Search Report dated Dec. 18, 2018 for Application No. 18196953.6, 15 pages.
(Continued)

*Primary Examiner* — Robert F Long
*Assistant Examiner* — Eduardo R Ferrero
(74) *Attorney, Agent, or Firm* — Frost Brown Todd LLC

(57) ABSTRACT

An apparatus includes an anvil, a closure assembly, a firing assembly, and a casing assembly. The firing assembly includes a staple driver and an annular array of staples. The casing assembly includes a first section and a second section. The first section includes a first handle portion, a first shaft portion, and a tubular casing. The tubular casing slidably houses the staple driver. The first section defines a homogenous continuum of material along the length of the first handle portion, the first shaft portion, and the tubular casing. The second section includes a second handle portion and a second shaft portion. The second handle portion is laterally coupled with the first handle portion. The second shaft portion is laterally coupled with the first shaft portion. The second section defines a homogenous continuum of material along the length of the second handle portion and the second shaft portion.

14 Claims, 26 Drawing Sheets

(51) Int. Cl.
*A61B 17/00* (2006.01)
*A61B 90/00* (2016.01)

(52) U.S. Cl.
CPC ............... *A61B 2017/00477* (2013.01); *A61B 2090/0811* (2016.02)

(58) Field of Classification Search
USPC ...................................................... 227/179.1
See application file for complete search history.

(56) References Cited

U.S. PATENT DOCUMENTS

| | | | | |
|---|---|---|---|---|
| 4,319,576 | A * | 3/1982 | Rothfuss | A61B 17/115 227/175.3 |
| 4,505,272 | A * | 3/1985 | Utyamyshev | A61B 17/115 227/155 |
| 4,576,167 | A * | 3/1986 | Noiles | A61B 17/115 227/179.1 |
| 4,646,745 | A * | 3/1987 | Noiles | A61B 17/115 227/178.1 |
| 5,005,749 | A * | 4/1991 | Aranyi | A61B 17/115 227/175.1 |
| 5,119,983 | A * | 6/1992 | Green | A61B 17/115 227/179.1 |
| 5,205,459 | A | 4/1993 | Brinkerhoff et al. | |
| 5,271,544 | A | 12/1993 | Fox et al. | |
| 5,275,322 | A | 1/1994 | Brinkerhoff et al. | |
| 5,285,945 | A | 2/1994 | Brinkerhoff et al. | |
| 5,292,053 | A | 3/1994 | Bilotti et al. | |
| 5,333,773 | A | 8/1994 | Main et al. | |
| 5,350,104 | A | 9/1994 | Main et al. | |
| 5,431,645 | A * | 7/1995 | Smith | A61B 18/1445 606/1 |
| 5,454,825 | A * | 10/1995 | Van Leeuwen | A61B 17/11 227/175.1 |
| 5,497,934 | A * | 3/1996 | Brady | A61B 17/072 227/176.1 |
| 5,533,661 | A | 7/1996 | Main et al. | |
| 5,685,474 | A | 11/1997 | Seeber | |
| 5,799,857 | A * | 9/1998 | Robertson | A61B 17/115 227/175.2 |
| 5,839,639 | A * | 11/1998 | Sauer | A61B 17/115 227/175.1 |
| 6,063,095 | A * | 5/2000 | Wang | A61B 34/75 128/898 |
| 7,794,475 | B2 | 9/2010 | Hess et al. | |
| 8,011,554 | B2 * | 9/2011 | Milliman | A61B 17/115 227/175.1 |
| 8,091,756 | B2 * | 1/2012 | Viola | A61B 17/07207 227/178.1 |
| 8,231,042 | B2 * | 7/2012 | Hessler | A61B 17/1114 227/179.1 |
| 8,322,590 | B2 * | 12/2012 | Patel | A61B 17/115 227/176.1 |
| 8,430,292 | B2 * | 4/2013 | Patel | A61B 17/115 227/181.1 |
| 8,453,914 | B2 * | 6/2013 | Laurent | A61B 17/068 227/179.1 |
| 8,910,847 | B2 | 12/2014 | Nalagatla et al. | |
| 9,289,207 | B2 | 3/2016 | Shelton, IV | |
| 9,463,022 | B2 | 10/2016 | Swayze et al. | |
| 9,498,222 | B2 | 11/2016 | Scheib et al. | |
| 9,532,783 | B2 | 1/2017 | Swayze et al. | |
| 9,572,573 | B2 | 2/2017 | Scheib et al. | |
| 9,597,081 | B2 | 3/2017 | Swayze et al. | |
| 9,713,469 | B2 * | 7/2017 | Leimbach | A61B 17/1155 |
| 9,724,100 | B2 | 8/2017 | Scheib et al. | |
| 2006/0049231 | A1 | 3/2006 | Leiboff et al. | |
| 2007/0034667 | A1 * | 2/2007 | Holsten | A61B 17/11 227/176.1 |
| 2007/0075117 | A1 * | 4/2007 | Milliman | A61B 17/115 227/179.1 |
| 2008/0015617 | A1 | 1/2008 | Harari et al. | |
| 2008/0142566 | A1 * | 6/2008 | Gresham | A61B 17/115 227/179.1 |
| 2008/0249546 | A1 | 10/2008 | Sandstrom et al. | |
| 2009/0152324 | A1 * | 6/2009 | Holsten | A61B 17/068 227/176.1 |
| 2011/0261666 | A1 | 10/2011 | Vlutters et al. | |
| 2012/0080492 | A1 * | 4/2012 | Scirica | A61B 17/0644 227/176.1 |
| 2012/0080498 | A1 * | 4/2012 | Shelton, IV | A61B 17/00491 227/178.1 |
| 2012/0138658 | A1 * | 6/2012 | Ullrich | A61B 17/072 227/175.1 |
| 2012/0168487 | A1 * | 7/2012 | Holsten | A61B 17/00491 227/176.1 |
| 2012/0193398 | A1 * | 8/2012 | Williams | A61B 17/0644 227/179.1 |
| 2012/0292372 | A1 | 11/2012 | Nalagatla et al. | |
| 2012/0292373 | A1 | 11/2012 | Nalagatla et al. | |
| 2013/0026209 | A1 * | 1/2013 | Mozdzierz | A61B 17/1155 227/180.1 |
| 2013/0172929 | A1 * | 7/2013 | Hess | F16B 15/00 606/219 |
| 2013/0175315 | A1 * | 7/2013 | Milliman | A61B 17/1155 227/175.1 |
| 2013/0175319 | A1 * | 7/2013 | Felder | A61B 17/1155 227/175.2 |
| 2014/0158747 | A1 | 6/2014 | Measamer et al. | |
| 2014/0305988 | A1 * | 10/2014 | Boudreaux | A61B 17/068 227/175.3 |
| 2014/0336665 | A1 * | 11/2014 | Gavala | A61B 17/22012 606/128 |
| 2015/0083773 | A1 | 3/2015 | Measamer et al. | |
| 2015/0351761 | A1 * | 12/2015 | Shelton, IV | A61B 17/00491 606/219 |
| 2016/0089141 | A1 * | 3/2016 | Harris | A61B 17/072 227/176.1 |
| 2016/0374671 | A1 | 12/2016 | Measamer et al. | |
| 2016/0374684 | A1 | 12/2016 | Dinardo et al. | |
| 2017/0055996 | A1 * | 3/2017 | Baxter, III | A61B 17/0644 |
| 2017/0128123 | A1 | 5/2017 | Williams et al. | |
| 2017/0281162 | A1 * | 10/2017 | Shelton, IV | A61B 17/115 |

OTHER PUBLICATIONS

Extended European Search Report dated Mar. 29, 2019 for Application No. 18196953.6, 13 pages.
International Search Report and Written Opinion dated Mar. 28, 2019 for International Application No. PCT/IB2018/057296, 23 pages.

* cited by examiner

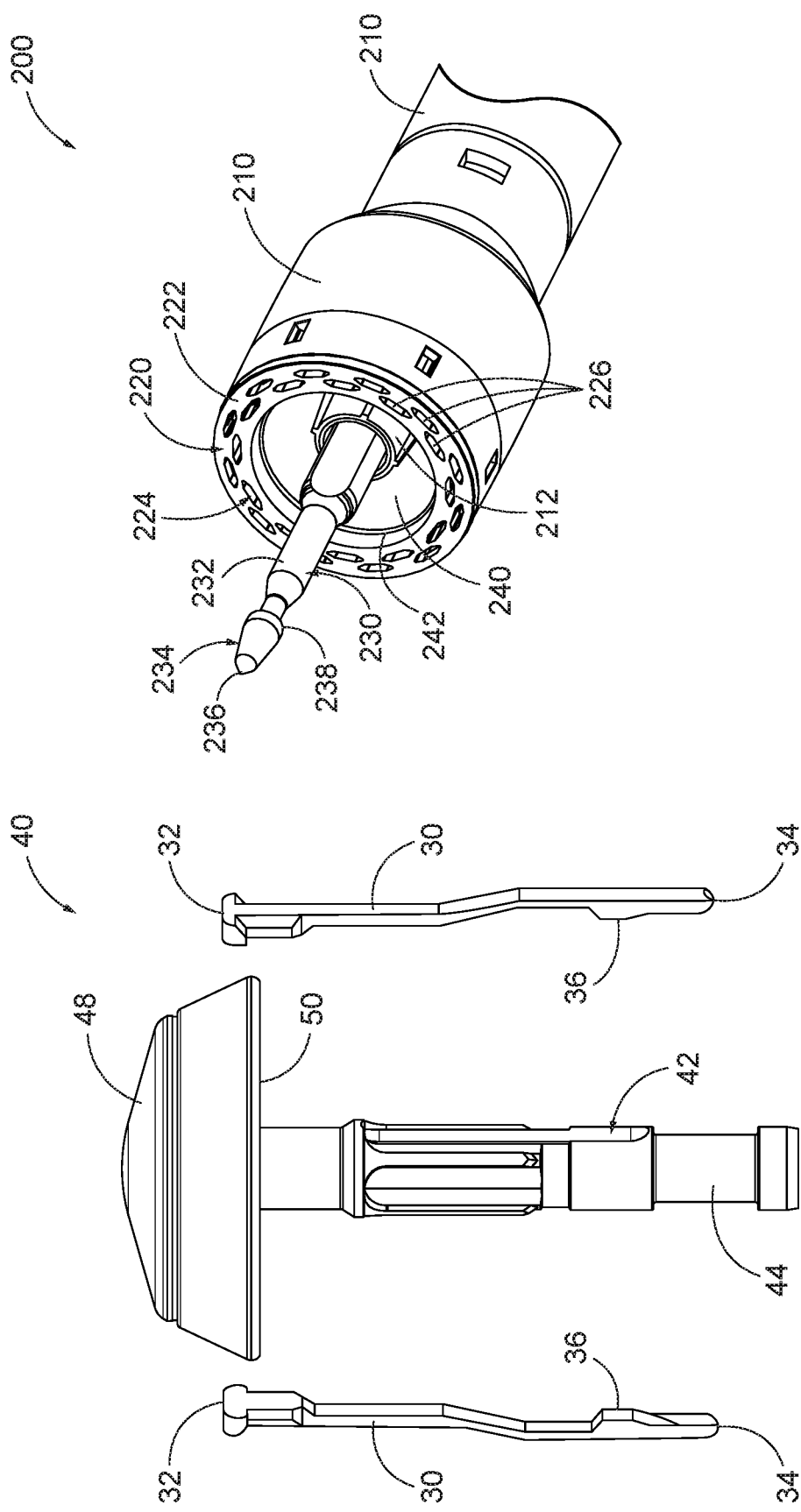

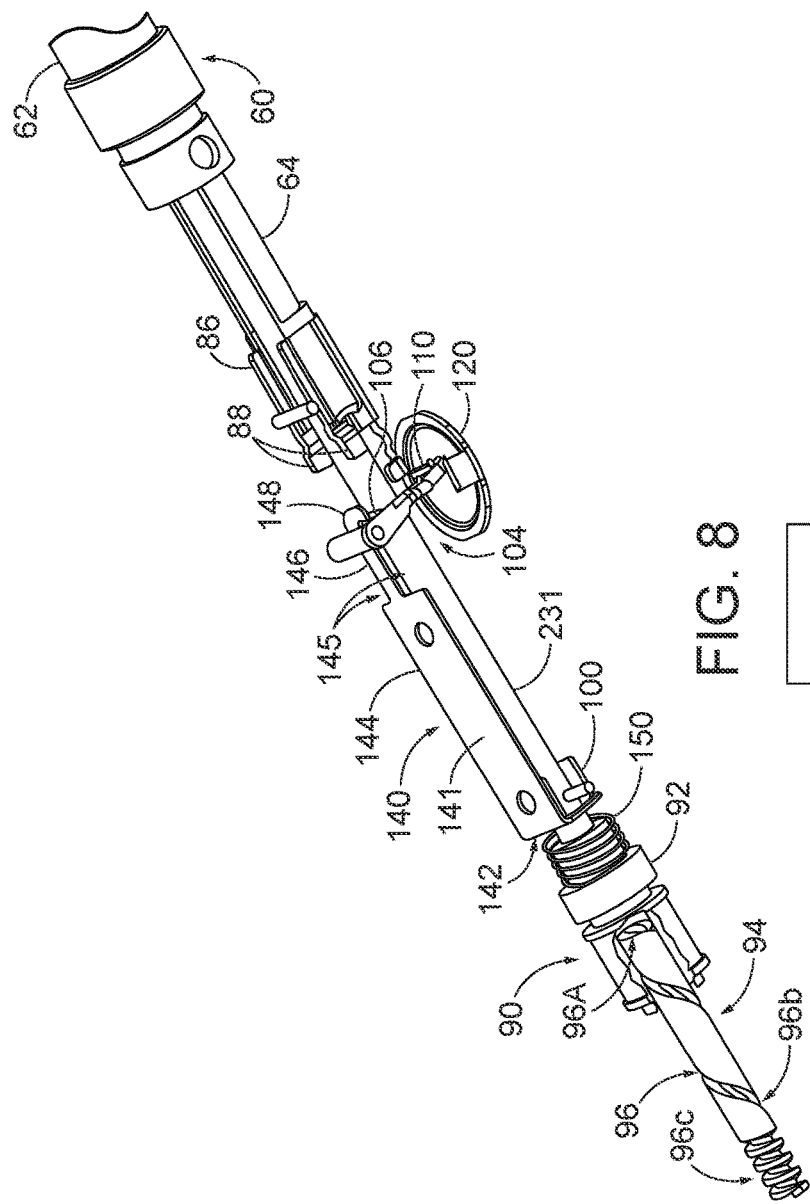
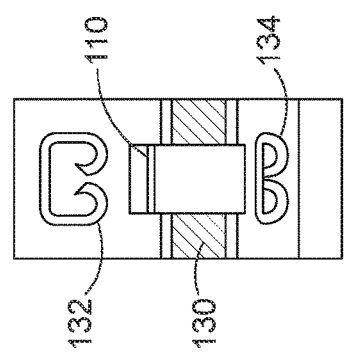

CIRCULAR STAPLING INSTRUMENT WITH ASYMMETRIC MOLDED SHROUD COMPONENTS

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts an exploded side elevational view of the anvil of FIG. 2;

FIG. 5 depicts a perspective view of a stapling head assembly of the surgical instrument of FIG. 1;

FIG. 8 depicts an enlarged partial perspective view of an exemplary indicator assembly of the surgical instrument of FIG. 1, showing an indicator window and indicator lever;

FIG. 9 depicts a diagrammatic view of the indicator window of FIG. 8, showing an exemplary indicator bar and exemplary corresponding staple representations;

Figure 1:
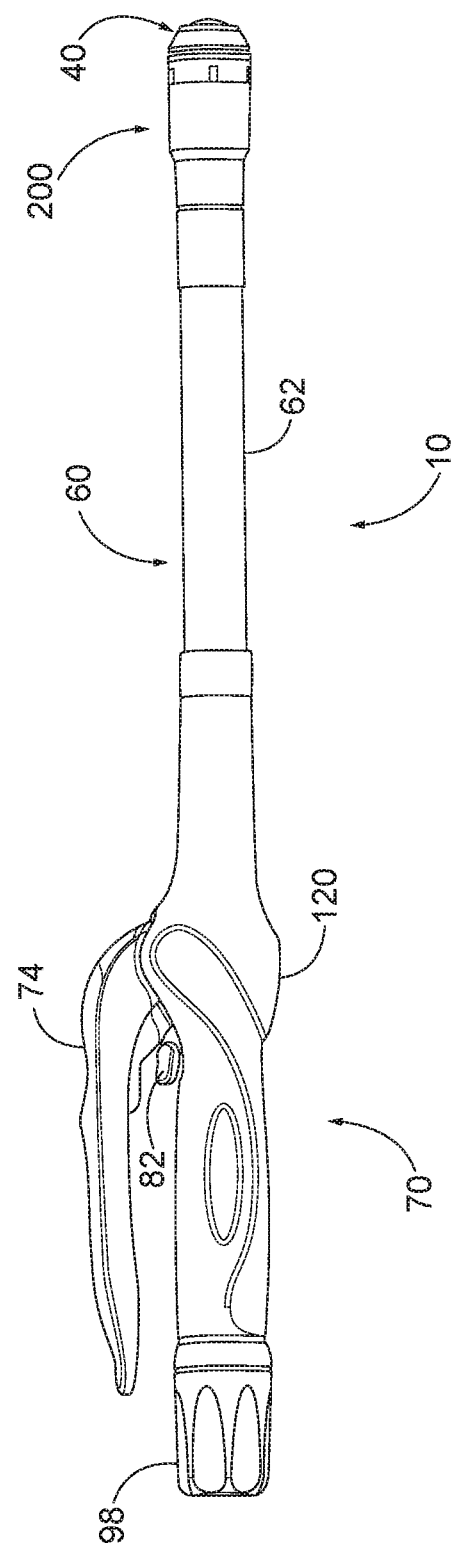
FIG. 1 depicts a side elevation view of an exemplary circular stapling surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-11 depict an exemplary circular surgical stapling instrument (10) having a stapling head assembly (200), a shaft assembly (60), and an actuator handle assembly (70), each of which will be described in more detail below. Shaft assembly (60) extends distally from actuator handle assembly (70) and stapling head assembly (200) is coupled to a distal end of shaft assembly (60). In brief, actuator handle assembly (70) is operable to actuate a staple driver member (250) of stapling head assembly (200) to drive a plurality of staples (66) out of stapling head assembly (200). Staples (66) are bent to form completed staples by an anvil (40) that is selectively attached at the distal end of instrument (10). Accordingly, tissue (2), as shown in FIGS. 10A-10E, may be stapled utilizing instrument (10).

In the present example, instrument (10) comprises a closure system and a firing system. As will be described in greater detail below, the closure system and anvil (40) are operable to clamp tissue between anvil (40) and stapling head assembly (200). As will also be described in greater detail below, the firing system and anvil (40) are operable to cut and staple tissue clamped between anvil (40) and stapling head assembly (200).

The closure system comprises a trocar (230), a trocar actuator (231), and an adjustment knob (98). Anvil (40) may be coupled to a distal end of trocar (230). Adjustment knob (98) is operable to longitudinally translate trocar (230) relative to stapling head assembly (200), thereby translating anvil (40) when anvil (40) is suitably coupled to trocar (230), and further clamping tissue between anvil (40) and stapling head assembly (200) as will be described in greater detail below.

The firing system comprises a trigger (74), a trigger actuation assembly (84), a driver actuator (64), and a staple driver member (250). Staple driver member (250) includes a knife member (240) configured to sever tissue when staple driver member (250) is actuated longitudinally. In addition, staples (66) are positioned distal to a plurality of staple drivers of staple driver member (250) such that staple driver member (250) also drives staples (66) distally when staple driver member (250) is actuated longitudinally. Thus, when trigger (74) is actuated and trigger actuation assembly (84) actuates staple driver member (250) via driver actuator (64), knife member (240) and staple drivers (252) substantially simultaneously sever tissue (2) and drive staples (66) distally relative to stapling head assembly (200) into tissue. The components and functionalities of the closure system and firing system will now be described in greater detail.

A. Exemplary Anvil

In the following discussion of anvil (40), the terms "distal" and "proximal" (and variations thereof) will be used with reference to the orientation of anvil (40) when anvil (40) is coupled with shaft assembly (60) of instrument (10). Thus, proximal features of anvil (40) will be closer to the operator of instrument (10); while distal features of anvil (40) will be further from the operator of instrument (10).

Figure 3:
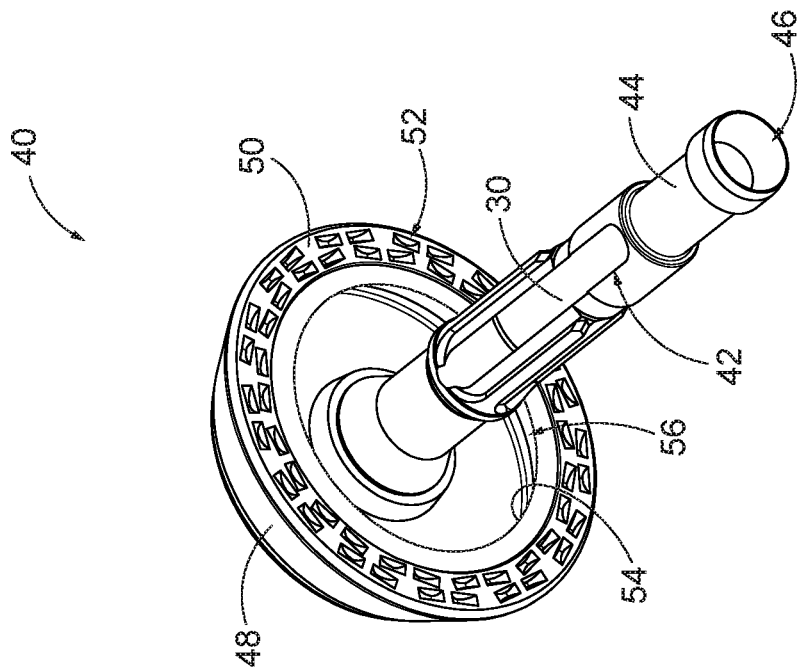
FIG. 3 depicts another perspective view of the anvil of FIG. 2.
Figure 2:
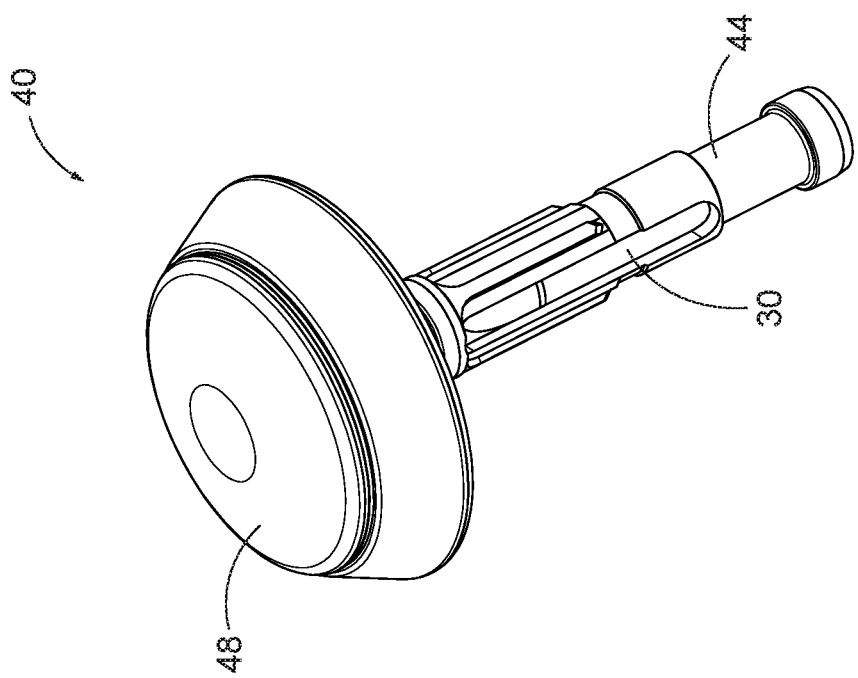
FIG. 2 depicts a perspective view of an exemplary anvil of the surgical instrument of FIG. 1.

As best seen in FIGS. 2-4, anvil (40) of the present example comprises a head (48) and a proximal shaft (44). As mentioned above and as will be described in greater detail below, anvil (40) of the present example may selectively couple to trocar (230) such that when coupled, movement of trocar (230) relative to stapling head assembly (200) also moves anvil (40) relative to stapling head assembly (200).

Head (48) includes a proximal surface (50) that defines a plurality of staple forming pockets (52). Staple forming pockets (52) are arranged in two concentric annular arrays. In some other versions, staple forming pockets (52) are arranged in three or more concentric annular arrays. Staple forming pockets (52) are configured to deform staples as the staples are driven into staple forming pockets (52). Accordingly, when anvil (40) is in the closed position and staples (66) are driven out of stapling head assembly (200) into staple forming pockets (52), each staple forming pocket (52) may deform a generally "U" shaped staple (66) into a "B" shape as is known in the art. As best seen in FIG. 4, proximal surface (50) terminates at an inner edge (54), which defines an outer boundary of an annular recess (56) surrounding proximal shaft (44).

Proximal shaft (44) defines a bore (46) and includes a pair of pivoting latch members (30) positioned in bore (46). As best seen in FIG. 4, each latch member (30) includes a "T" shaped distal end (32), a rounded proximal end (34), and a latch shelf (36) located distal to proximal end (34). "T" shaped distal ends (32) secure latch members (30) within bore (46). Latch members (30) are positioned within bore (46) such that distal ends (34) are positioned at the proximal ends of lateral openings (42), which are formed through the sidewall of proximal shaft (44). Lateral openings (42) thus provide clearance for distal ends (34) and latch shelves (36) to deflect radially outwardly from the longitudinal axis defined by proximal shaft (44). However, latch members (30) are configured to resiliently bias distal ends (34) and latch shelves (36) radially inwardly toward the longitudinal axis defined by proximal shaft (44). Latch members (30) thus act as retaining clip to allow anvil (40) to be selectively secured to trocar (230) of stapling head assembly (200). It should be understood, however, that latch members (36) are merely optional. Anvil (40) may be removably secured to a trocar (230) using any other suitable components, features, or techniques.

In addition to or in lieu of the foregoing, anvil (40) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847; U.S. Pub. No. 2016/0374671, issued as U.S. Pat. No. 10,188,386 on Jan. 29, 2019; and/or U.S. Pub. No. 2016/0374684, issued as U.S. Pat. No. 10,226,253 on Mar. 12, 2019, the disclosures of which are incorporated by reference herein. Still other suitable configurations will be apparent to one of ordinary skill in the art in view of the teachings herein.

B. Exemplary Stapling Head Assembly

Figure 6:
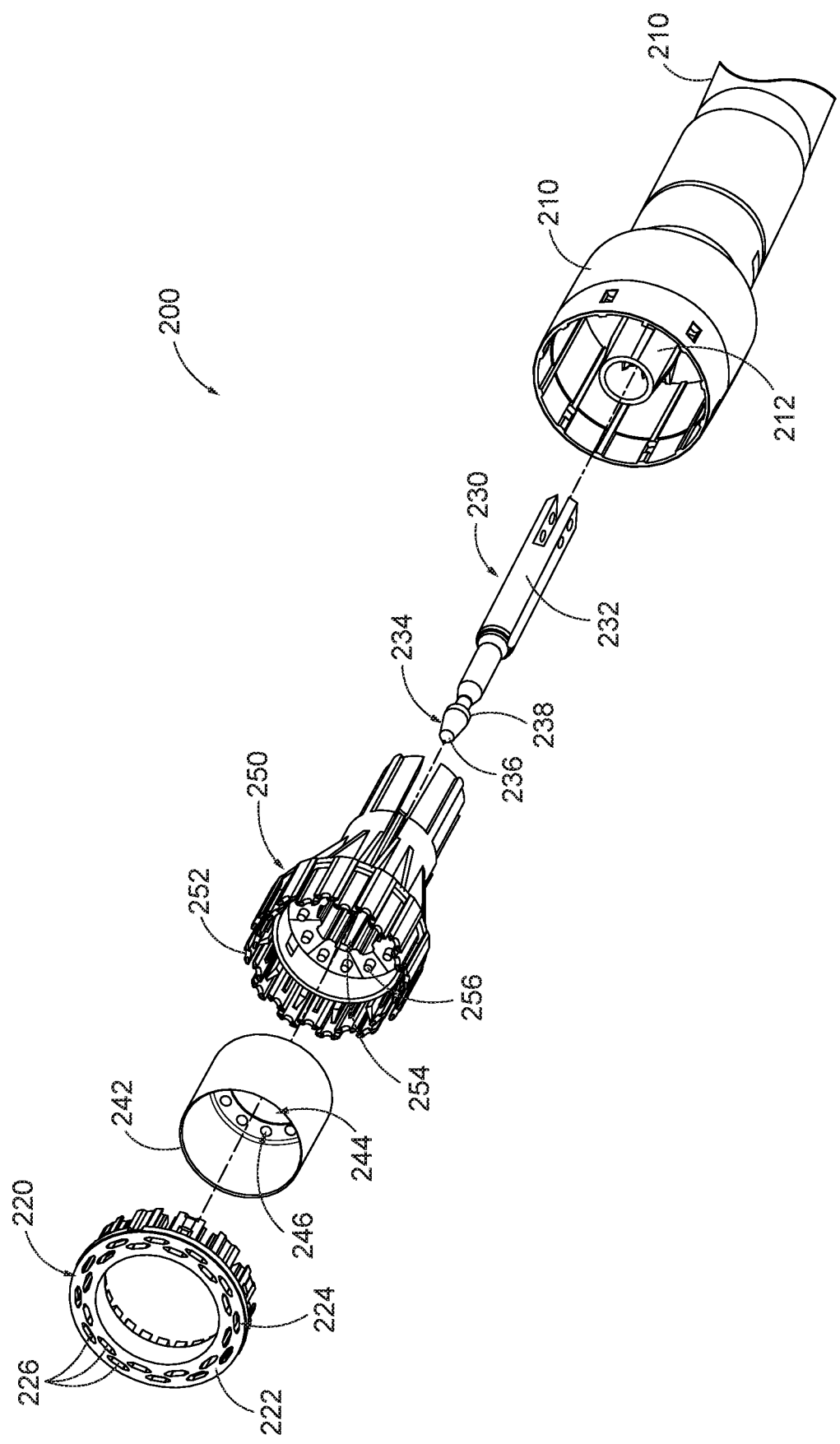
FIG. 6 depicts an exploded perspective view of the stapling head assembly of FIG. 5.

As best seen in FIGS. 5-6, stapling head assembly (200) of the present example is coupled to a distal end of shaft assembly (60) and comprises a tubular casing (210) housing a slidable staple driver member (250). A cylindraceous inner core member extends distally within tubular casing (210). Tubular casing (210) is fixedly secured to an outer sheath (62) of shaft assembly (60), such that tubular casing (210) serves as a mechanical ground for stapling head assembly (200).

Trocar (230) is positioned coaxially within inner core member (212) of tubular casing (210). As mentioned above and as will be described in greater detail below, trocar (230) is operable to translate distally and proximally relative to tubular casing (210) in response to rotation of adjustment knob (98) relative to casing (110) of handle assembly (100). Trocar (230) comprises a shaft (232) and a head (234). Head (234) includes a pointed tip (236) and an inwardly extending proximal surface (238). Shaft (232) thus provides a reduced outer diameter just proximal to head (234), with surface (238) providing a transition between that reduced outer diameter of shaft (232) and the outer diameter of head (234). While tip (236) is pointed in the present example, tip (236) is not sharp. Tip (236) will thus not easily cause trauma to tissue due to inadvertent contact with tissue. Head (234) and the distal portion of shaft (232) are configured for insertion in bore (46) of anvil (40). Proximal surface (238) and latch shelves (36) have complementary positions and configurations such that latch shelves (36) engage proximal surface (238) when proximal shaft (44) of anvil (40) is fully seated on trocar (230). Anvil (40) may thus secure to trocar (230) through a snap fitting between latch members (30) and head (234). In addition, or in the alternative, trocar (230) may include a magnetic portion (not shown) which may attract anvil (40) towards trocar (230). Still further configurations and arrangements for anvil (40) and trocar (230) will be apparent to one of ordinary skill in the art in view of the teachings herein.

Figure 10A:
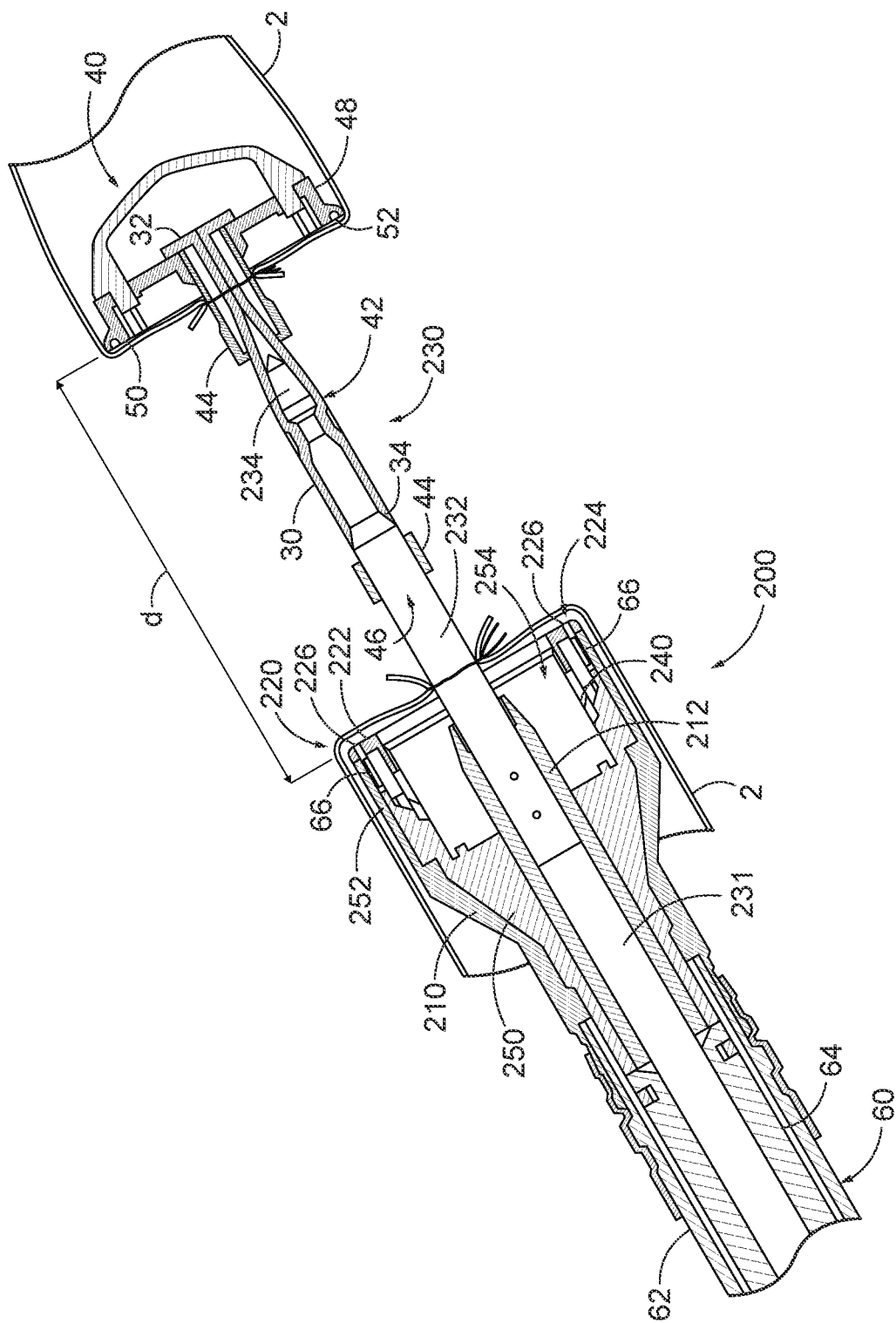
FIG. 10A depicts an enlarged longitudinal cross-section view of the stapling head assembly of FIG. 5, showing the anvil of FIG. 2 in a first open position, where the anvil is within a first tubular portion of tissue and the stapling head assembly is within a second tubular portion of tissue.
Figure 10B:
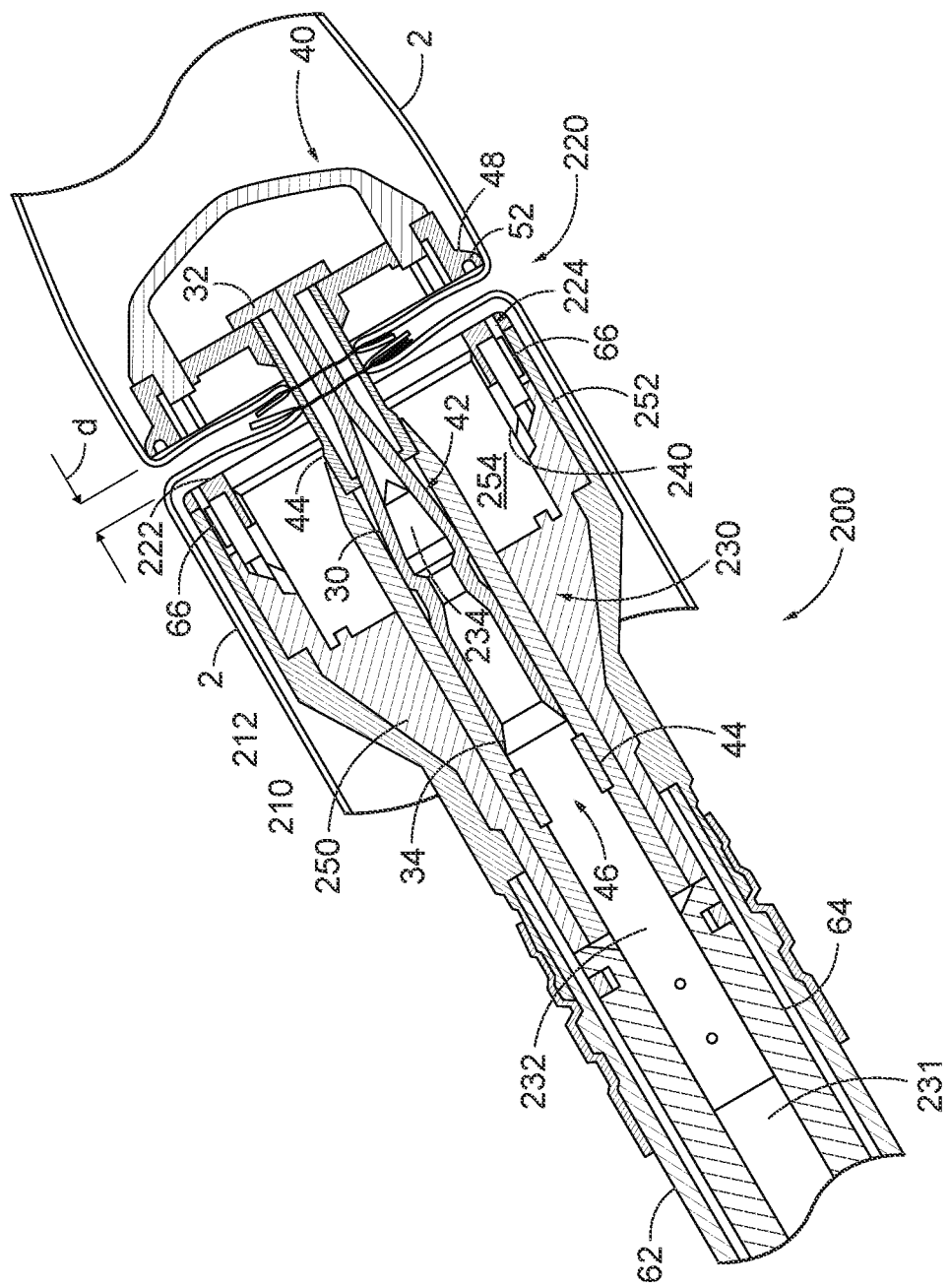
FIG. 10B depicts an enlarged longitudinal cross-sectional view of the stapling head assembly of FIG. 5, showing the anvil of FIG. 2 in a closed position, where the anvil is within the first tubular portion of tissue and the stapling head assembly is within the second tubular portion of tissue.

Staple driver member (250) is operable to actuate longitudinally within tubular casing (210) in response to rotation of trigger (74) of actuator handle assembly (70) as will be described in greater detail below. Staple driver member (250) includes two distally presented concentric annular arrays of staple drivers (252). Staple drivers (252) are arranged to correspond with the arrangement of staple forming pockets (52) described above. As best seen in FIGS. 10A-10B, each staple driver (252) is located underneath a corresponding staple (66). The arrangement of staple drivers (252) may be modified just like the arrangement of staple forming pockets (52) as described above. Staple driver member (250) also defines a bore (254) that is configured to coaxially receive core member (212) of tubular casing (210). An annular array of studs (256) project distally from a distally presented surface surrounding bore (254).

A cylindraceous knife member (240) is coaxially positioned within staple driver member (250). Knife member (240) includes a distally presented, sharp circular cutting edge (242). Knife member (240) is sized such that knife member (240) defines an outer diameter that is smaller than the diameter defined by the inner annular array of staple drivers (252). Knife member (240) also defines an opening that is configured to coaxially receive core member (212) of tubular casing (210). An annular array of openings (246) formed in knife member (240) is configured to complement the annular array of studs (256) of staple driver member (250), such that knife member (240) is fixedly secured to staple driver member (250) via studs (256) and openings (346). Therefore, when stapling driver member (250) is actuated relative to tubular casing (210), so is knife member (240). Other suitable structural relationships between knife member (240) and stapler driver member (250) will be apparent to those of ordinary skill in the art in view of the teachings herein.

A deck member (220) is fixedly secured to tubular casing (210). Deck member (220) includes a distally presented deck surface (222) defining two concentric annular arrays of staple openings (224), where each staple opening (224) has its own staple pocket (226) housing a staple (66). Staple openings (224) and staple pockets (226) are arranged to correspond with the arrangement of staple drivers (252) and staple forming pockets (52) described above. Accordingly, when staple driver member (250) is actuated distally relative to tubular casing (210) in response to rotation of trigger (74), each staple driver (252) drives a corresponding staple (66) out of its staple pocket (226) and through a corresponding staple opening (224) of deck member (220). When anvil (40) is in the closed position, staples (66) are driven into a corresponding staple forming pockets (52) to bend legs (68) of the staples (66), thereby stapling the material located between anvil (40) and stapling head assembly (200).

The arrangement of staple openings (224) may be modified just like the arrangement of staple forming pockets (52) as described above. It should also be understood that various structures and techniques may be used to contain staples (66) within stapling head assembly (200) before stapling head assembly (200) is actuated. Such structures and techniques that are used to contain staples within stapling head assembly (200) may prevent the staples from inadvertently falling out through staple openings (224) before stapling head assembly (200) is actuated. Various suitable forms that such structures and techniques may take will be apparent to those of ordinary skill in the art in view of the teachings herein.

As best seen in FIG. 6, deck member (220) defines an inner diameter that is just slightly larger than the outer diameter defined by knife member (240). Deck member (220) is thus configured to allow knife member (240) to translate distally to a point where cutting edge (242) is distal to deck surface (222).

In addition to or in lieu of the foregoing, stapling head assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847; U.S. Pub. No. 2016/0374671, issued as U.S. Pat. No. 10,188,386 on Jan. 29, 2019; and/or U.S. Pub. No. 2016/0374684, issued as U.S. Pat. No. 10,266,253 on Mar. 12, 2019 the disclosures of which are incorporated by reference herein. Still other suitable configurations will be apparent to one of ordinary skill in the art in view of the teachings herein.

C. Exemplary Shaft Assembly

Figure 7A:
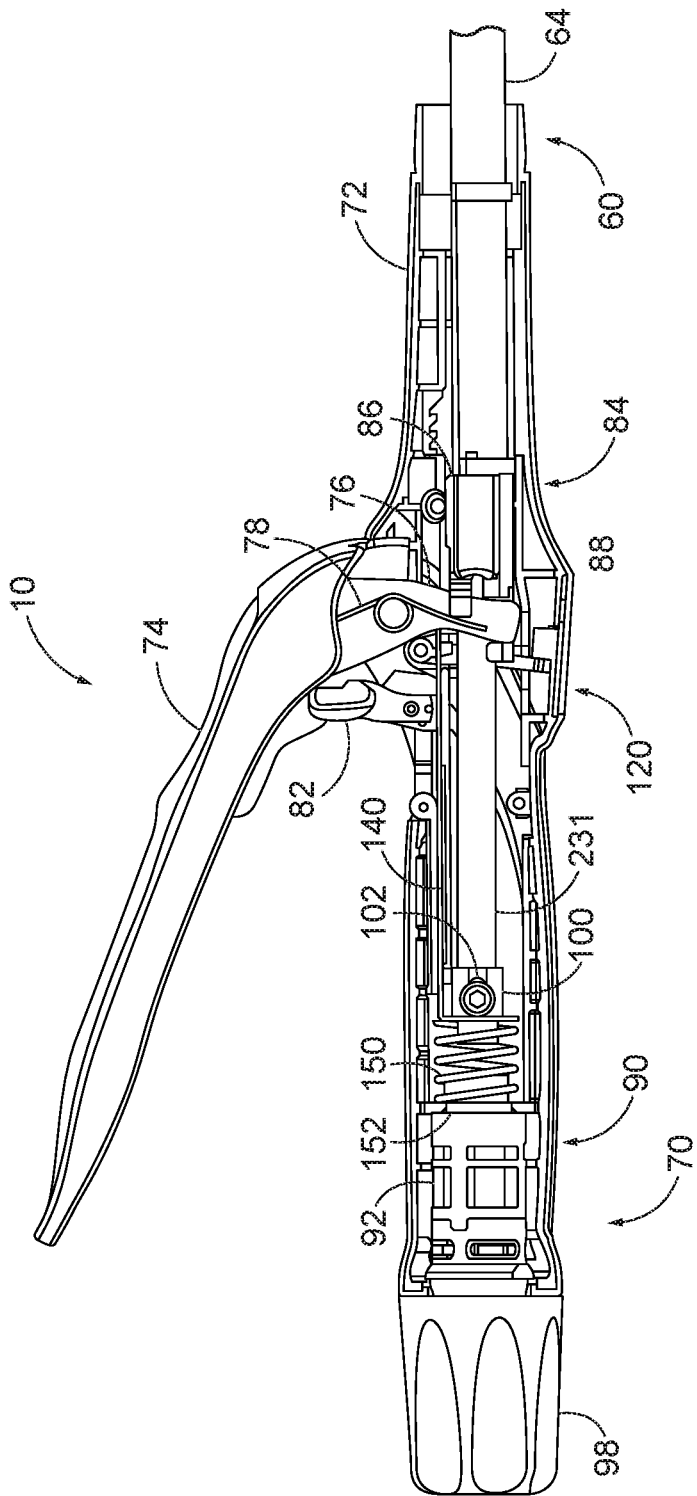
FIG. 7A depicts an enlarged side elevation view of an exemplary actuator handle assembly of the surgical instrument of FIG. 1 with a portion of the body removed, showing a trigger in an unfired position and a lockout feature in a locked position.
Figure 7B:
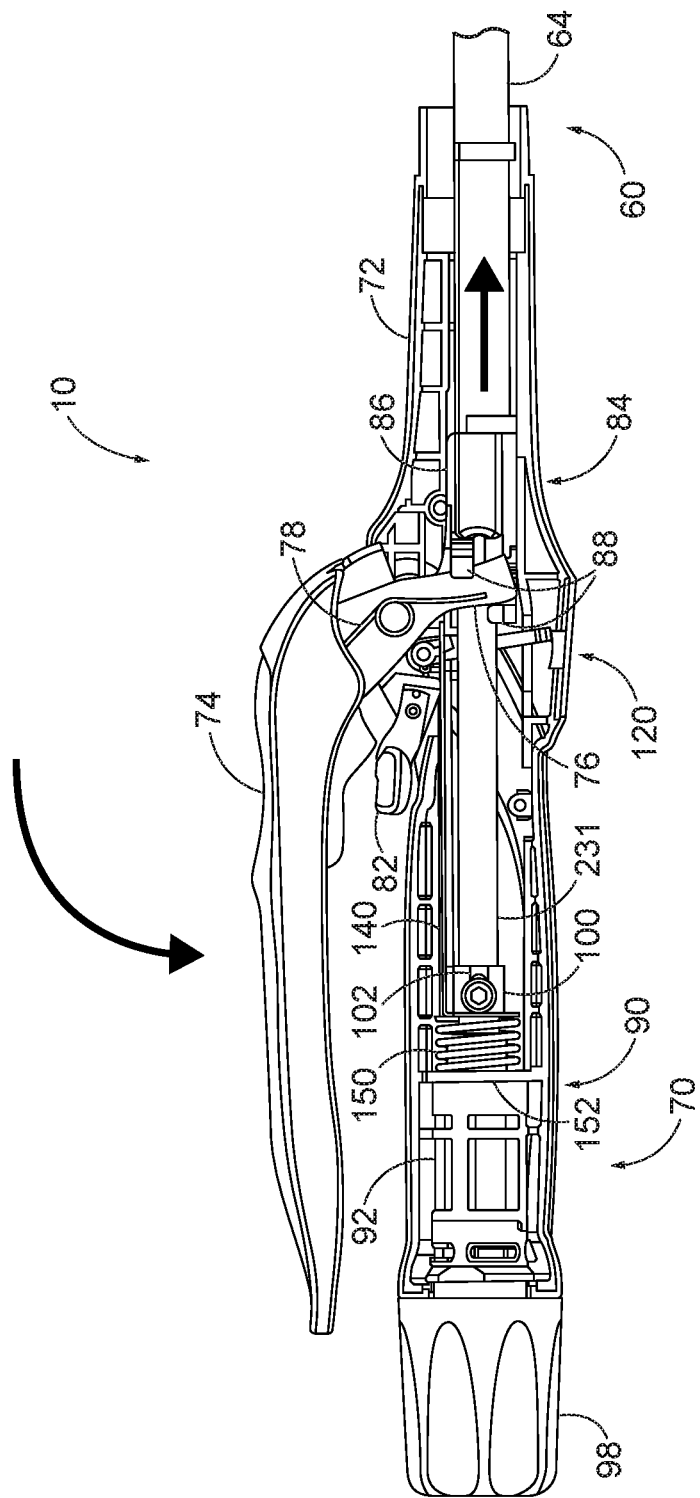
FIG. 7B depicts an enlarged side elevation view of the actuator handle assembly of FIG. 7A, showing the trigger in a fired position and the lockout feature in an unlocked position.

Stapling head assembly (200) and trocar (230) are positioned at a distal end of shaft assembly (60), as shown in FIGS. 10A-10D. Shaft assembly (60) of the present example comprises an outer tubular member (62) and a driver actuator (64). Outer tubular member (62) is coupled to tubular casing (210) of stapling head assembly (200) and to a body (72) of actuator handle assembly (70), thereby providing a mechanical ground for the actuating components therein. As seen in FIGS. 7A-7B, the proximal end of driver actuator (64) is coupled to a trigger actuation assembly (84) of actuator handle assembly (70), as described below. The distal end of driver actuator (64) is coupled to staple driver member (250) such that the rotation of trigger (74) longitudinally actuates staple driver member (250). As shown in FIGS. 10A-10D, driver actuator (64) comprises a tubular member having an open longitudinal axis such that trocar actuator (231), which is coupled to trocar (230), may actuate longitudinally within and relative to driver actuator (64). Other components may be disposed within driver actuator (64) as will be apparent to one of ordinary skill in the art in view of the teachings herein.

In the present example, shaft assembly (60) is substantially straight. However, shaft assembly (60) may extend distally from actuator handle assembly (70) with a preformed bend. In some versions, the preformed bend is configured to facilitate positioning of stapling head assembly (200) within a patient's colon. Various suitable bend angles or radii that may be used will be apparent to those of ordinary skill in the art in view of the teachings herein. In examples where shaft assembly (60) includes a preformed bend, actuator (231) may be coupled with trocar (230) via a flexible band portion (not shown). Flexible band portion (not shown) may extend from a distal end of actuator (231), located proximal to the preformed bend, to couple with trocar (230), located distal to the preformed bend. Flexible band portion (not shown) may be dimensioned to flex during translation along the longitudinal profile of the preformed bend of shaft assembly (60). In such cases, trocar actuator (231) may be slidably housed within actuator handle assembly (70), while trocar (230) is slidably housed within tubular casing (210). Flexible band portion (not shown) may be connected to both trocar (230) and actuator (231) via pins.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661; U.S. Pub. No. 2012/0292372, issued as U.S. Pat. No. 8,910,847 on Dec. 16, 2014; and/or U.S. Pub. No. 2015/0083773, issued as U.S. Pat. No. 9,936,949 on Apr. 10, 2018, the disclosures of which are incorporated by reference herein; and/or in accordance with other configurations as will be apparent to one of ordinary skill in the art in view of the teachings herein.

D. Exemplary Actuator Handle Assembly

Referring now to FIGS. 7A-8, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 7A) to a fired position (shown in FIG. 7B) actuates driver actuator (64) described above. A spring (78) is coupled to body (72) and trigger (74) to bias trigger (74) towards the unfired position. Lockout feature (82) is a pivotable member that is coupled to body (72). In a first, locked position, as shown in FIG. 7A, lockout feature (82) is pivoted upwards and away from body (72) such that lockout feature (82) engages trigger (74) and mechanically resists actuation of trigger (74) by a user. In a second, unlocked position, such as that shown in FIGS. 1 and 7B, lockout feature (82) is pivoted downward such that trigger (74) may be actuated by the user. Accordingly, with lockout feature (82) in the second position, trigger (74) can engage a trigger actuation assembly (84) to fire instrument F.

As shown in FIGS. 7A-7B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661; U.S. Pub. No. 2012/0292372, issued as U.S. Pat. No. 8,910,847 on Dec. 16, 2014; and/or U.S. Pub. No. 2015/0083773, issued as U.S. Pat. No. 9,936,949 on Apr. 10, 2019, the disclosures of which are incorporated by reference herein; and/or in accordance with other configurations as will be apparent to one of ordinary skill in the art in view of the teachings herein.

Body (72) also houses trocar actuation assembly (90) configured to actuate trocar (230) longitudinally in response to rotation of adjustment knob (98). As best shown in FIGS. 7A-8, trocar actuation assembly (90) of the present example comprises adjustment knob (98), a grooved shank (94), and a sleeve (92). Grooved shank (94) of the present example is located at a proximal end of trocar actuator (231). In other versions, grooved shank (94) and trocar actuator (231) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (not shown). Adjustment knob (98) also defines internal threading (not shown) as will be described in greater detail below. Grooved shank (94) of the present example comprises a continuous groove (96) formed in the outer surface of grooved shank (94). Accordingly, when adjustment knob (98) is rotated, the internal tab of sleeve (92) rides within groove (96) and grooved shank (94) is longitudinally actuated relative to sleeve (92). Since grooved shank (94) is located at the proximal end of trocar actuator (231), rotating adjustment knob (98) in a first direction advances trocar actuator (231) distally relative to actuator handle assembly (70). When trocar (230) is coupled with anvil (40), anvil (40) also advances distally relative to stapling head assembly (200) thereby increasing the distance between proximal surface (50) of the anvil (40) and distally presented deck surface (222) of deck member (220), otherwise known as a gap distance d. By rotating adjustment knob (98) in the opposite direction, trocar actuator (231) is actuated proximally relative to actuator handle assembly (70) to reduce the gap distance d between anvil (40) and stapling head assembly (200) when trocar (230) is coupled with anvil (40). Thus, trocar actuation assembly (90) is operable to actuate trocar (230) in response to rotating adjustment knob (98). Other suitable configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial length of grooved shank (94). Middle portion (96B) comprises a section with comparably coarser pitch or fewer grooves per axial length such that relatively few rotations are required for the internal tab of sleeve (92) to traverse along axial distance. When anvil (40) is in an initial, distal position in relation to stapling head assembly (200) (as shown in FIG. 10A) the internal tab of sleeve (92) is positioned in middle portion (96B). Accordingly, the gap distance d may be quickly reduced through relatively few rotations of adjustment knob (98) while the internal tab of sleeve (92) traverses middle portion (96B). Proximal portion (96C) of the present example is substantially like distal portion (96A) and comprises a fine pitch or a high number of grooves over a short axial distance of grooved shank (94) such that many rotations are required to traverse the short axial distance. Proximal portion (96C) of the present example is engaged by the internal threading defined by knob (98) when anvil (40) is substantially near to stapling head assembly (200) (as shown in FIG. 10B), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages the internal threading of knob (98), each rotation of adjustment knob (98) may reduce the gap distance d by a relatively small amount to provide for fine tuning. The internal tab of sleeve (92) may be disengaged from groove (96) when proximal portion (96C) is engaged with the internal threading of knob (98).

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2015/0083773, issued as U.S. Pat. No. 9,936,949 on Apr. 10, 2018, the disclosures of which are incorporated by reference herein; and/or in accordance with other configurations as will be apparent to one of ordinary skill in the art in view of the teachings herein.

As noted above, gap distance d corresponds to the distance between anvil (40) and stapling head assembly (200). When instrument (10) is inserted into a patient, this gap distance d may not be easily viewable. Accordingly, a moveable indicator bar (110), shown in FIGS. 8-9, is provided to be visible through an indicator window (120) positioned opposite to trigger (74). As will be described in greater detail below, indicator bar (110) is operable to move in response to rotation of adjustment knob (98) such that the position of indicator bar (110) is representative of the gap distanced. As shown in FIG. 9, indicator window (120) further comprises a scale (130) which indicates that the anvil gap is within a desired operating range (e.g., a green colored region or "green zone") and a corresponding staple compression representation at each end of scale (130). By way of example only, as shown in FIG. 9, a first staple image (132) depicts a large staple height while a second staple image (134) depicts a small staple height. Accordingly, a user can view the position of the coupled anvil (40) relative to the stapling head assembly (200) via indicator bar (110) and scale (130). The user may then adjust the positioning of anvil (40) via adjustment knob (98) accordingly.

In the example shown in FIGS. 7A-8, a U-shaped clip (100) is attached to an intermediate portion of trocar actuator (231) located distally of grooved shank (94). In the present example, an extension of trocar actuator (231) engages a slot in the housing of handle assembly (70) to prevent trocar actuator (231) from rotating about its axis when adjustment knob (98) is rotated.

Because trocar actuator (231) and trocar (230) are two separate components joined together during assembly, a tolerance stack may occur once trocar (230) and trocar actuator (231) are assembled and suitably incorporated into instrument (10). To accommodate for this potential tolerance stack, it may be necessary to calibrate the proper placement of trocar actuator (231) within instrument (10) such that indicator bar (110) may show a proper gap distance d during exemplary use. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (231) for purposes of calibrating indicator bar (110) relative to scale (130). In some versions, the attachment member (e.g., screw, bolt, pin, etc.) engages with a portion of body (72) to substantially prevent trocar actuator (231) from rotating about its axis when adjustment knob (98) is rotated.

As shown in FIG. 8, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (231) and/or grooved shank (94). A coil spring (150) is interposed between flange (142) and a boss (152) to bias flange (142) against U-shaped clip (100). Accordingly, when U-shaped clip (100) actuates distally with trocar actuator (231) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (231) and/or grooved shank (94) translate proximally, thereby compressing coil spring (150). In some versions indicator bracket (140) may be fixedly attached to trocar actuator (231) and/or grooved shank (94).

In the present example, a portion of lockout feature (82) abuts a surface (141) of indicator bracket (140) when indicator bracket (140) is in a longitudinal position that does not correspond to when gap distance d is within a desired operating range (e.g., a green colored region or "green zone"). When gap distance d is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between proximal surface (50) of anvil (40) and distally presented deck surface (222) of deck member (220).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, issued as U.S. Pat. No. 8,910,847 on Dec. 16, 2014; and/or U.S. Pub. No. 2015/0083773, issued as U.S. Pat. No. 9,936,949 on Apr. 10, 2018, the disclosures of which are incorporated by reference herein; and/or in accordance with other configurations as will be apparent to one of ordinary skill in the art in view of the teachings herein.

E. Exemplary Use of Circular Stapling Surgical Instrument

FIGS. 7A-7B and FIGS. 10A-10E show an exemplary use of circular stapling surgical instrument (10) in accordance with the description above. As mentioned above, anvil (40) may selectively couple with trocar (230) such that movement of trocar (230) relative to tubular casing (210) and deck member (220) leads to movement of anvil (40) relative to tubular casing (210) and deck member (220). With anvil (40) as a separate component, it should be understood that anvil (40) may initially be inserted and secured to a portion of tissue (2) prior to being coupled with trocar (230). By way of example only, anvil (40) may be inserted into and secured to a first tubular portion of tissue (2) while stapling head assembly (200) is inserted into and secured to a second tubular portion of tissue (2). For instance, the first tubular portion of tissue (2) may be sutured to or about a portion of anvil (40), and the second tubular portion of tissue (2) may be sutured to or about trocar (230).

As shown in FIG. 10A, anvil (40) may then be coupled to trocar (230) in accordance with the description above, such as a snap fitting between latch members (30) of anvil (40) and head (234) of trocar (230). In FIG. 10A, trocar (230) is shown in a distal most actuated position. Trocar (230) may be actuated to the distal most actuated position by rotation of knob (98) in accordance with the description above. Such an extended position for trocar (230) may provide a larger area to which tissue (2) may be coupled prior to attachment of anvil (40). The extended position of trocar (230) may also provide for easier attachment of anvil (40) to trocar (230). At the position shown in FIG. 10A, trigger (74) is locked in the position shown in FIG. 7A by lockout feature (82), as lockout feature (82) may not pivot to unlock trigger (74) due to interference caused by surface (141) of indicator bracket (140) in accordance with the description above.

As mentioned above, when anvil (40) is coupled to trocar (230), rotation of adjustment knob (98) may translate both trocar (230) and anvil (40), thereby enlarging or reducing gap distanced. For instance, as shown sequentially in FIGS. 10A-10B, anvil (40) is shown actuating proximally relative to actuator handle assembly (70) from an initial, open position (FIG. 10A) to a closed position (FIG. 10B) where gap distance d is brought within a suitable predetermined range. When gap distance d is brought within a suitable predetermined range, indicator bar (110) may move within indicator window (120) to show the relative gap distance d is within a desired operating range (e.g. a green colored region or "green zone") in accordance with the description above. Additionally, shown between FIGS. 7A-7B, when gap distance d is brought within a suitable predetermined range, lockout feature (82) may be pivoted relative to body (72) to an unlocked position and trigger (74) may pivot relative to body (72) to engage trigger actuation assembly (84) in accordance with the description above.

Figure 10C:
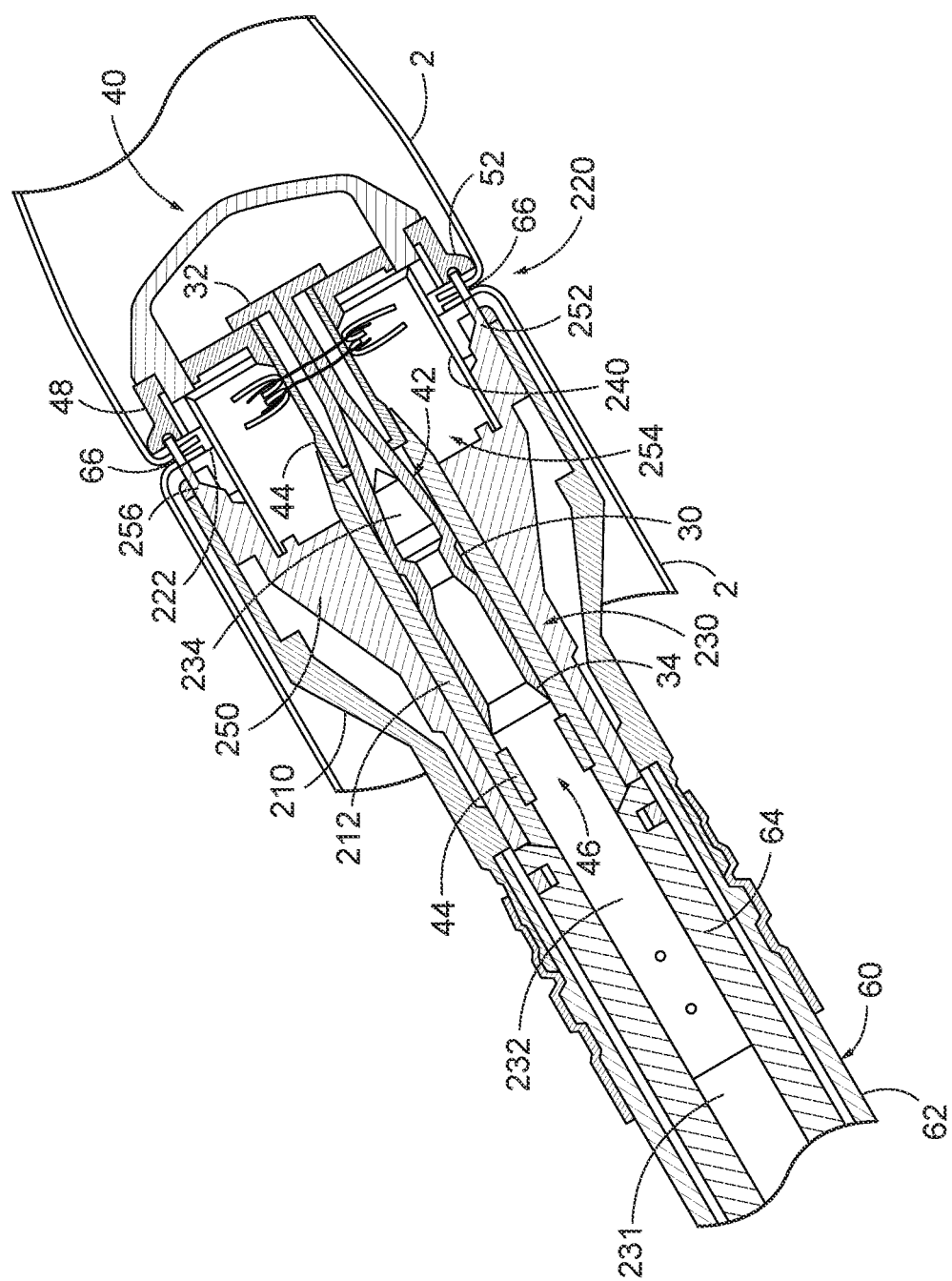
FIG. 10C depicts an enlarged longitudinal cross-sectional view of the stapling head assembly of FIG. 5, showing the anvil of FIG. 2 in the closed position, were an exemplary staple driver and blade are in a fired position such that the first tubular portion of tissue and the second tubular portion of tissue are stapled together with excess tissue severed.

As shown in FIG. 7B, with lockout feature (82) pivoted into the unlocked position, trigger (74) is pivoted toward body (72) such that trigger arms (76) drive against tabs (88) to distally actuate slidable trigger carriage (86) and driver actuator (64). As shown in FIG. 10C, distal actuation of driver actuator (64) drives slidable staple driver member (250), staples drivers (252), and cylindraceous knife member (240) distally. Distal advancement of staple drivers 9352) drive staples (66) against corresponding staple forming pockets (52) thereby stapling tissue (2) between anvil (40) and stapling head assembly (200) to form a continuous tubular portion of tissue (2). Additionally, distal advancement of cylindraceous knife member (240) severs excess tissue located radially interior to newly formed staples (66). Stapling head assembly (200) is operable to staple and sever tissue (2) by a user pivoting a trigger (74) of actuator handle assembly (70), as will be described in greater detail below.

Figure 10D:
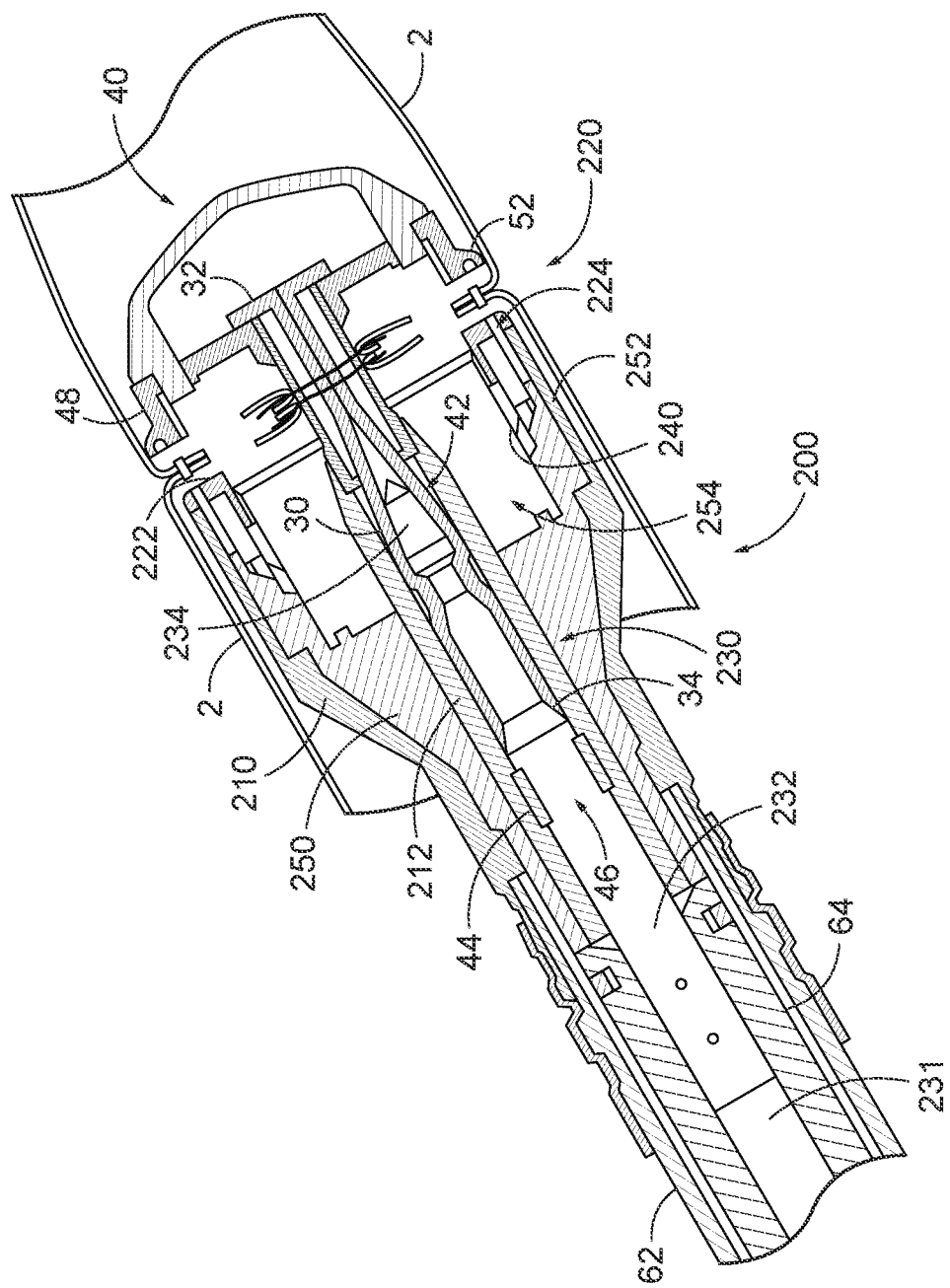
FIG. 10D depicts an enlarged longitudinal cross-sectional view of the stapling head assembly of FIG. 5, showing the anvil of FIG. 2 in a second open position, where the first tubular portion of tissue and the second tubular portion of tissue are attached.
Figure 10E:
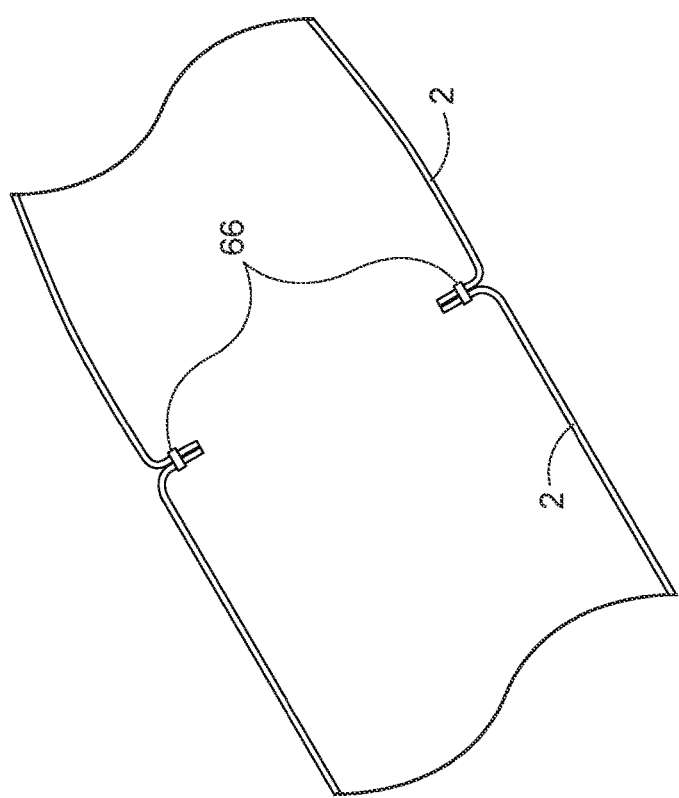
FIG. 10E depicts an enlarged longitudinal cross-section view of the first tubular portion and the second tubular portion after the stapling head assembly of FIG. 5 and the anvil of FIG. 2 have been removed, leaving a completed end-to-end anastomosis.
Figure 11:
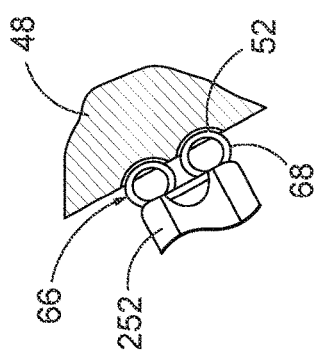
FIG. 11 depicts an enlarged partial cross-sectional view of an exemplary staple formed against the anvil of FIG. 2.

As best shown in FIG. 10D, once trigger (74) has been actuated to staple and sever tissue (2), a user may then turn rotatable knob (98) to distally advance anvil (40), thereby releasing portions of tissue (2) grasped between proximal surface (50) of anvil (40) and distally presented deck surface (222) of deck member (220). As best shown in FIG. 10E, with previously grasped tissue (2) released, a user may then remove instrument (10), thereby leaving a continuous tubular portion of tissue (2) behind.

II. Exemplary Alternative Circular Stapling Surgical Instrument

As mentioned above, outer tubular member (62) of shaft assembly (60) is coupled to tubular casing (210) of stapling head assembly (200) and to a body (72) of actuator handle assembly (70), thereby providing a mechanical ground for the actuating components therein. However, tissue (2) captured between anvil (40) and deck member (220) may require high compressive forces to ensure gap distance d is within a desired operating range. Because deck member (220) is fixed to tubular casing (210), these high compressive forces are transferred from deck member (220) to tubular casing (210), tubular member (62), and body (72). Since tubular casing (210), tubular member (62), and body (72) are coupled together as separate pieces, the high compressive forces associated with capturing tissue (2) between anvil (40) and deck member (220) may cause tubular casing (210), tubular member (62), and/or body (72) to compress relative to each other and/or to otherwise slightly move relative to each other, which may lead to an undesirable tolerance stack during exemplary use. An undesirable tolerance stack in components forming the mechanical ground during use may lead to an uncertain gap distance d, or otherwise adversely affect the quality of an anastomosis formed using staples. Therefore, it may be desirable to have an instrument having capabilities of providing a mechanical ground with consistent dimensions during use.

A. Overview of Exemplary Circular Stapling Surgical Instrument

Figure 12:
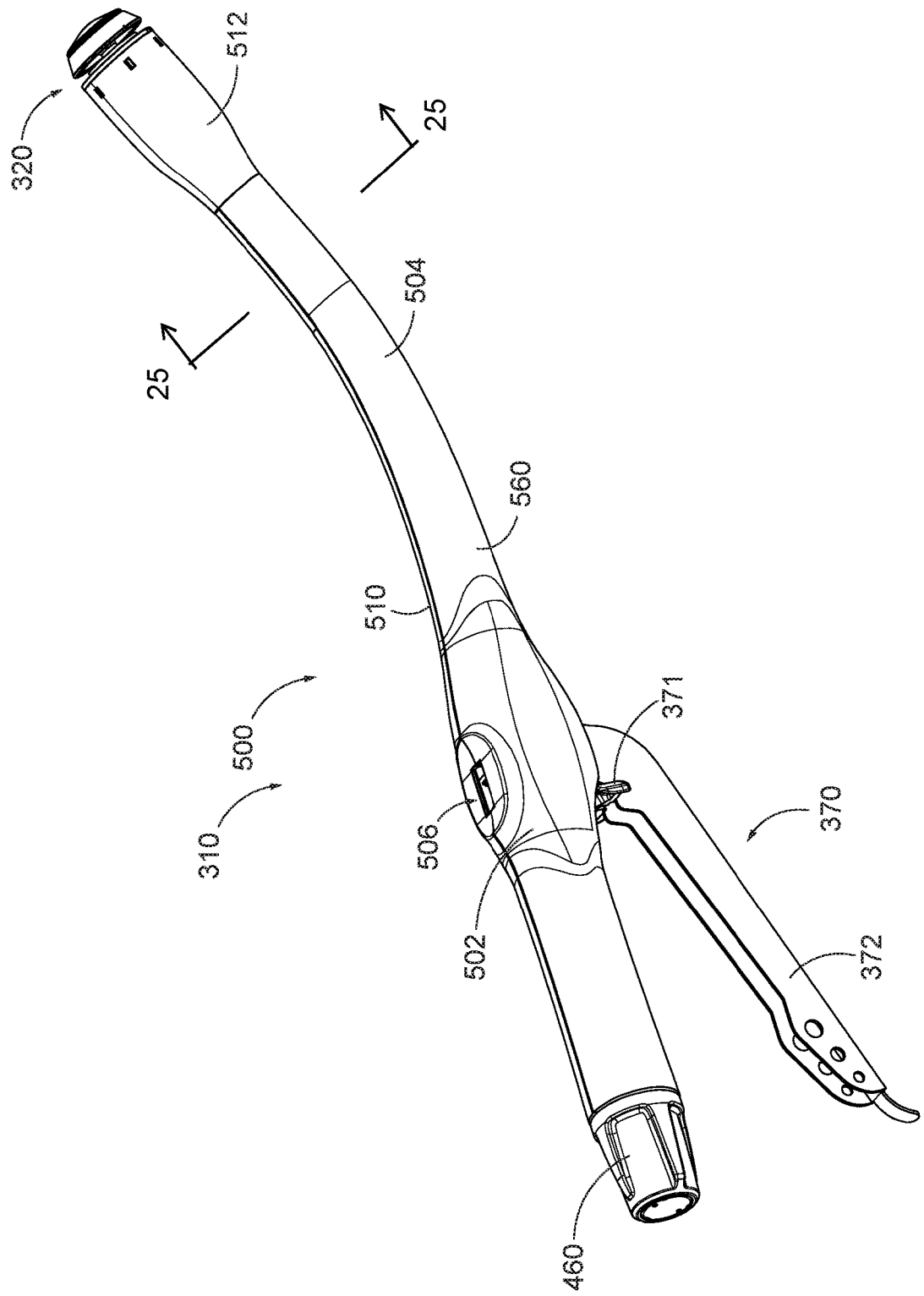
FIG. 12 depicts a perspective view of an exemplary alternative circular stapling surgical instrument.
Figure 13:
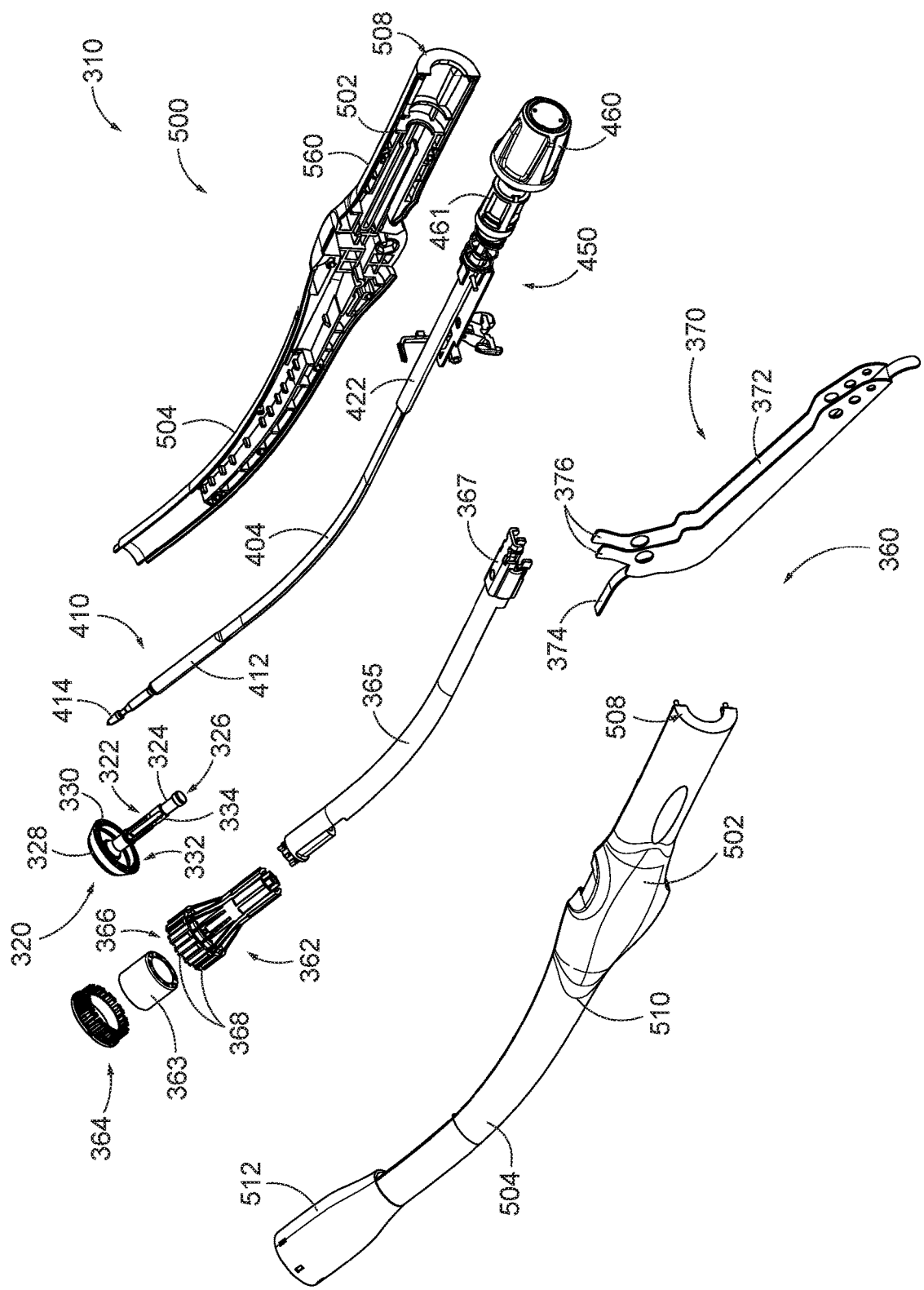
FIG. 13 depicts an exploded perspective view of the surgical instrument of FIG. 12.

FIGS. 12-13 show an exemplary circular stapling surgical instrument (310) that may be used in replacement of instrument (10) described above. Therefore, instrument (310) may perform substantially similarly as instrument (10) describe above, with differences described below. Instrument (310) includes an anvil (320), a firing system (360), a closure system (400), and a casing assembly (500). In brief, closure system (400) and anvil (320) are operable to clamp tissue between anvil (320) and a deck member (364) of firing system (360); while firing system (360) and anvil (40) are operable to cut and staple tissue clamped between anvil (320) and deck member (364). As will be described in greater detail below, casing assembly (500) is configured to provide a consistently dimensioned mechanical ground for actuating components during use of instrument (310).

Anvil (320) is substantially like anvil (40) described above. Therefore, Anvil (320) includes a proximal shaft (324), an anvil head (328), and a pair of pivoting latch members (334); which are substantially like proximal shaft (44), anvil head (48), and pivoting latch members (30) described above, respectively. Therefore, proximal shaft (44) defines a pair of lateral openings (322) and a bore (326), which are substantially like lateral openings (42) and bore (46) described above, respectively. Anvil head (328) includes a proximal surface (330) defining a plurality of staple forming pockets (332); which are substantially like proximal surface (50) and stapling forming pockets (52) described above.

Figure 15:
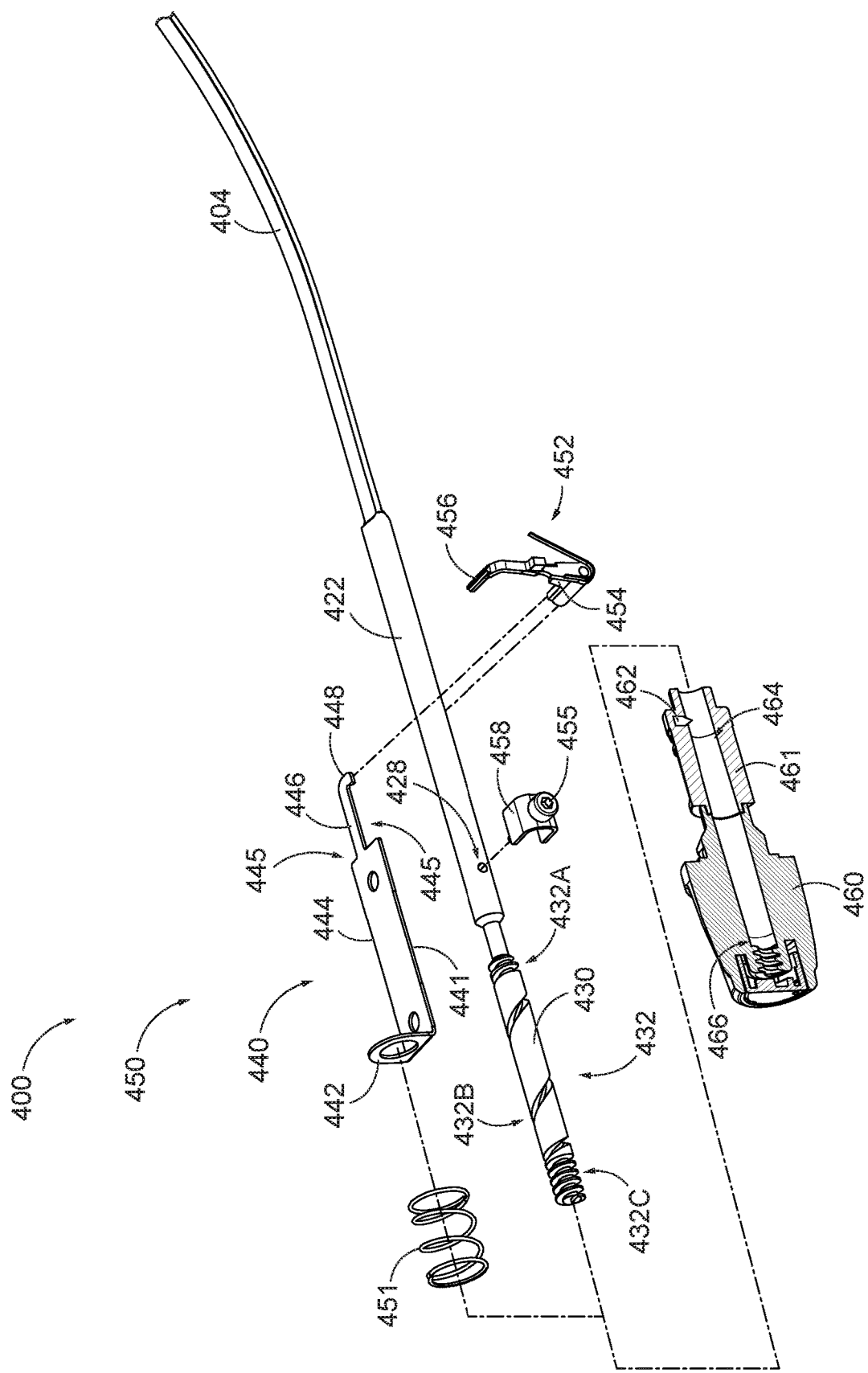
FIG. 15 depicts an exploded perspective view of the closure system of FIG. 14.
Figure 16:
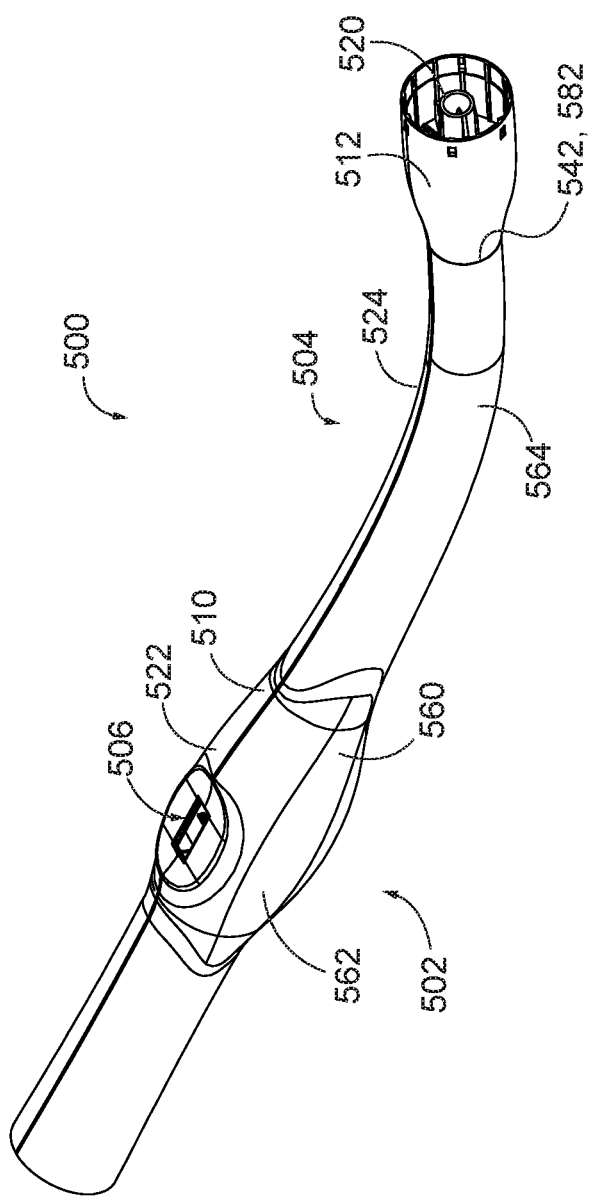
FIG. 16 depicts a perspective view of an exemplary casing assembly of the surgical instrument of FIG. 12.
Figure 17:
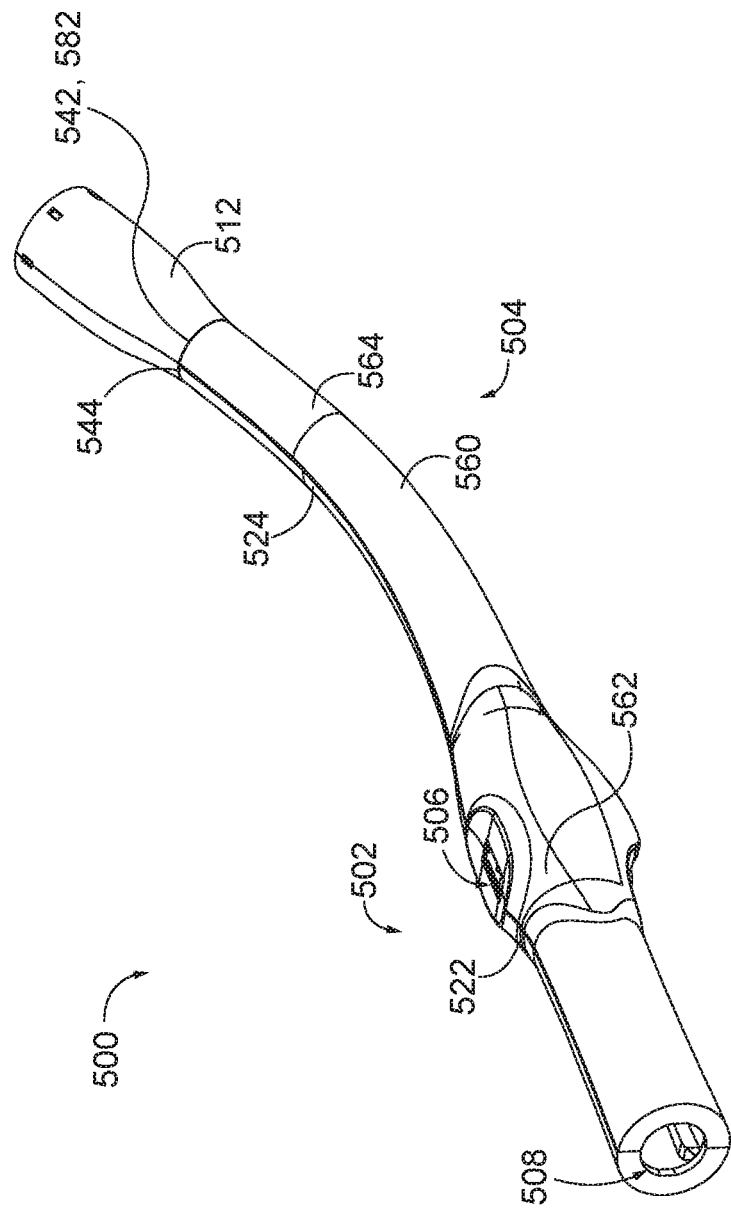
FIG. 17 depicts another perspective view of the casing assembly of FIG. 16.
Figure 18:
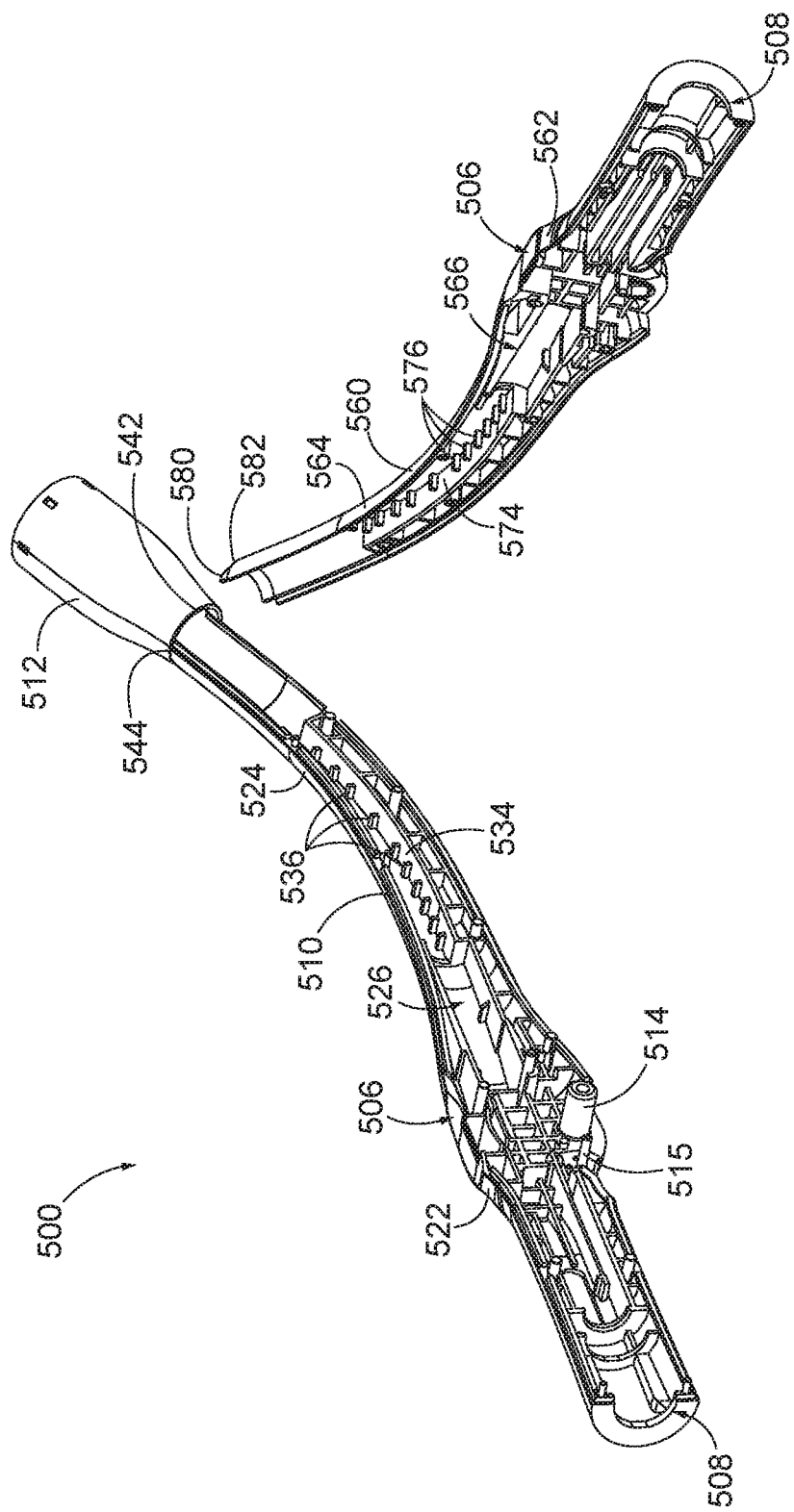
FIG. 18 depicts an exploded perspective view of the casing assembly of FIG. 16.

Closure system (400) includes monolithic closure rod (402), a gap indicator assembly (450), and an adjustment knob (460). Adjustment knob (460) is rotatably supported on a proximal end of casing assembly (500) such that adjustment knob (460) may rotate about its own longitudinal axis while remaining longitudinally stationary relative to casing assembly (500). Adjustment knob (460) includes a sleeve (461), which is substantially like sleeve (92) described above. As best seen in FIG. 15, adjustment knob (460) defines a distally open channel (464). Distally open channel (464) is dimensioned to slidably receive a proximal grooved section (430) of monolithic closure rod (402). Adjustment knob (460) includes an internal tab (462) extending within distally open channel (464) as well as an internal threading portion (466); which may be substantially similar internal tab and internal threading of adjustment knob (98) described above, respectively. Therefore, like adjustment knob (98) and grooves (96A, 96B) described above, internal tab (462) may mesh with grooves (432A, 432B) of proximal grooved section (430) such that rotation of internal tab (462) will translate monolithic closure rod (402) relative to casing assembly (500). Additionally, like adjustment knob (98) and groove (96C) described above, internal threading (466) may selectively engage with groove (432C) when monolithic closure rod (402) is translated proximal enough such that rotation of internal threading (466) may actuate monolithic closure rod (402) relative to casing assembly (500).

Gap indicator assembly (450) is configured to indicate through indicator window (506) a gap distance d between anvil (320) and deck member (364) during use of instrument (310). Gap indicator assembly (450) includes a spring (451), an indicator bracket (440), a U-shaped clip (458), and an indicator (452); which are substantially like spring (150), indicator bracket (140), U-shaped clip (100), and indicator (104) described above, respectively. Therefore, indicator bracket (440) includes an angled flange (442), a rectangular plate (444) having a surface (441), an indicator arm (446) defining gaps (445), and a laterally projecting finger (448); which are substantially like angled flange (142), rectangular plate (144) having surface (141), indicator arm (146) defining gaps (145), and laterally projecting finger (148) described above. Additionally, indicator (452) is pivotally mounted to casing assembly (500). Indicator (452) includes a tab (454), and an indicator bar (456); which are substantially like tab (106) and indicator bar (110) described above.

Like spring (150), U-shaped clip (100), and indicator bracket (140) described above, spring (451) biases angled flange (442) against U-shaped clip (458) while U-shaped clip (458) is attached to monolithic closure rod (402) via pin (455). Angled flange (442) is formed at the proximal end of rectangular plate (444) and includes an aperture to slidably mount onto monolithic closure rod (402). Therefore, as monolithic closure rod (402) is actuated distally, spring (451) will bias angled flange (442) distally to remain in engagement with U-shaped clip (458). Conversely, when monolithic closure rod (402) is actuated proximally, U-shaped clip (458) will push angled flange (442) further proximally, thereby compressing spring (451). In other words, spring (451) and U-shaped clip (458) interact with angled flange (442) such that indicator bracket (440) actuates with monolithic closure rod (402). In the present example, indicator bracket (440) is slidably attached to casing assembly (500). However, in some versions, indicator bracket (440) may be fixedly attached to monolithic closure rod (402).

In the present example, a portion of lockout feature (371) abuts a surface (441) of indicator bracket (440) when indicator bracket (440) is in a longitudinal position that does not correspond to when gap distance d is within a desired operating range (e.g., a green colored region or "green zone"). When gap distance d is within a desired operating range (e.g., a green colored region or "green zone"), indicator bracket (440) narrows to provide a pair of gaps (445) on either side of an indicator arm (446) that permits lockout feature (371) to pivot, thereby unlocking trigger (370). Accordingly, lockout feature (371) and indicator bracket (440) can substantially prevent a user from unlocking and operating trigger (370) until anvil (320) is in a predetermined operating range. Lockout feature (371) may be omitted entirely in some versions.

This operating range associated with the gap distance d may be visually communicated to the user via indicator bar (456) of indicator (452), shown against a scale (not shown) of indicator window (506), described briefly above. At the distal end of indicator bracket (440) is a distally projecting indicator arm (446) that terminates at a laterally projecting finger (448) for controlling the movement of indicator (452). Indicator arm (446) and finger (448) are configured to engage tab (454) of indicator (452) such that indicator (452) is pivoted when indicator bracket (440) is actuated longitudinally. In the present example, indicator (452) is pivotably coupled to casing assembly (500) at a first end of indicator (452), though this is merely optional and other pivot points for indicator (452) will be apparent to one of ordinary skill in the art in view of the teachings herein. Indicator bar (456) is positioned on the second end of indicator (452) such that indicator bar (456) moves in response to the actuation of indicator bracket (440). Accordingly, like indicator bar (110) described above, indicator bar (456) is displayed through an indicator window (506) against a set of indicia (not shown) to show the relative gap distance d between proximal surface (330) of anvil (320) and distally presented deck surface of deck member (364).

Figure 14:
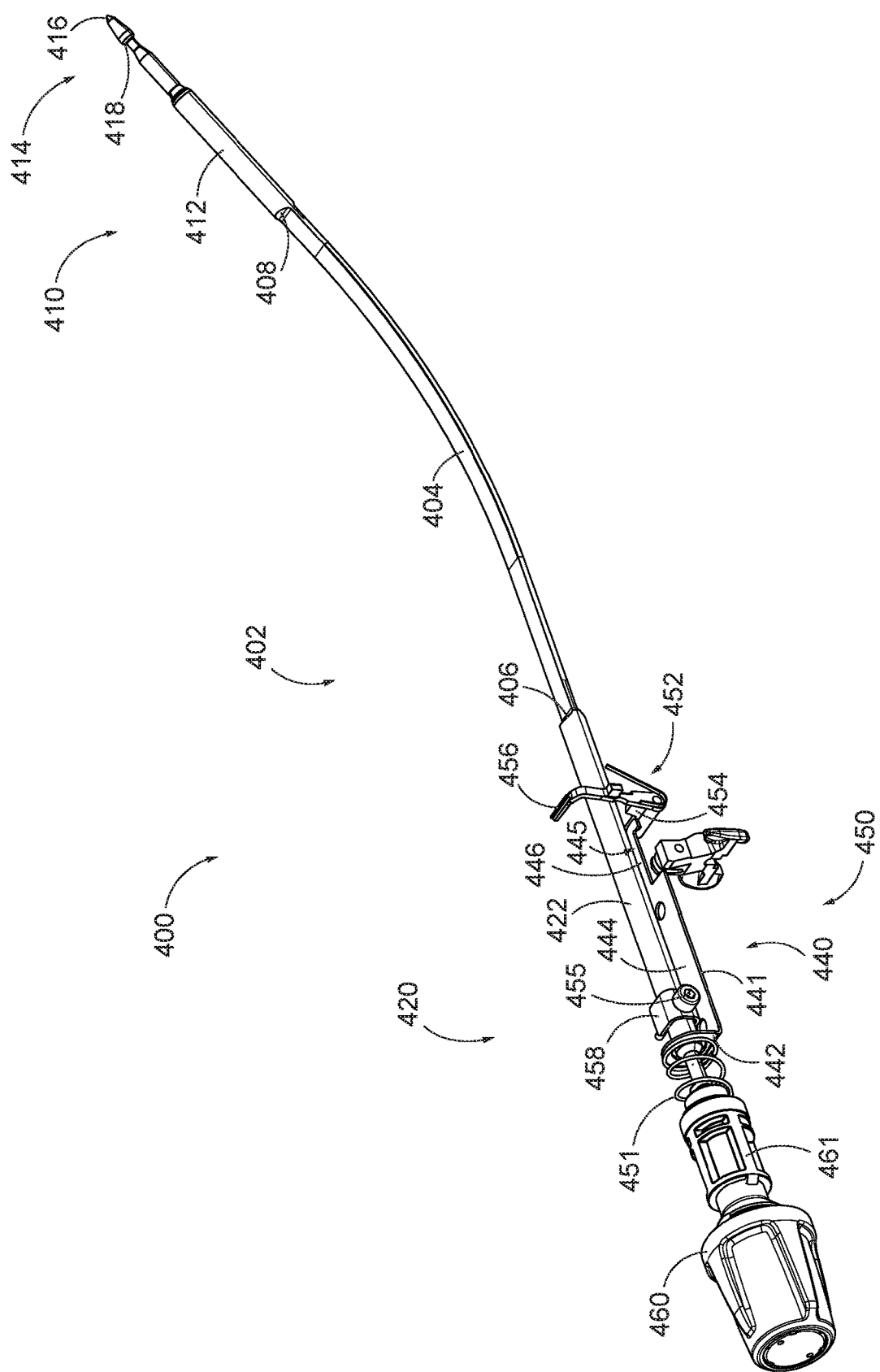
FIG. 14 depicts a perspective view of a closure system of the surgical instrument of FIG. 12.

As best seen in FIGS. 14-15, monolithic closure rod (402) includes proximal shank portion (420), a connecting band portion (404), and distal trocar portion (410). Distal trocar portion (410) includes a shaft (412) and a head (414), which may be substantially like shaft (232) and head (234) of trocar (230) described above. Distal trocar portion (410) is slidably housed within inner core member (520) of tubular casing (512). Distal trocar portion (410) may interact with anvil (320) in a substantially similar manner as trocar (230) and anvil (40), described above. Head (414) includes a pointed tip (416) and an inwardly extending proximal surface (418). Shaft (412) thus provides a reduced outer diameter just proximal to head (414), with surface (418) providing a transition between the reduced outer diameter of shaft (412) and the outer diameter of head (414). While tip (416) is pointed in the present example, tip (416) is not sharp. Tip (416) will thus not easily cause trauma to tissue due to inadvertent contact with tissue.

Proximal surface (418) of head (414) and latch shelves (340) of pivoting latch members (334) have complementary positions and configurations such that latch shelves (not shown) engage proximal surface (418) when proximal shaft (324) of anvil (320) is fully seated on distal trocar portion (410). Anvil (320) may thus secure to distal trocar portion (410) through a snap fitting between latch members (334) and head (414). In addition, or in the alternative, distal trocar portion (410) may include a magnetic portion (not shown) that may attract anvil (320) toward distal trocar portion (410). Still further configurations and arrangements for anvil (320) and distal trocar portion (410) will be apparent to one of ordinary skill in the art in view of the teachings herein.

Proximal shank portion (420) includes proximal grooved section (430) and a rod (422). Proximal shank portion (420) is slidably housed within handle portion (502) of casing assembly (500). Rod (422) defines a pin hole (428) that receives pin (455). As mentioned above, pin (455) couples U-shaped clip (458) of gap indicator assembly (450) to rod (422). Additionally, a portion of pin (455) may be slidably housed within a slot defined by casing assembly (500) such that rod (422), and therefore monolithic closure rod (402), is rotationally constrained about the longitudinal axis defined by monolithic closure rod (402); but also such that monolithic closure rode (402) may translate relative to casing assembly (500).

Proximal grooved section (430) of the present example comprises a continuous groove (432) formed in the outer surface of proximal grooved section (430). Accordingly, when adjustment knob (460) is rotated, internal tab (462) rides within continuous groove (432), and monolithic closure rod (402) is thereby longitudinally actuated relative to adjustment knob (460). Rotating adjustment knob (460) in a first direction advances monolithic closure rod (402) distally relative to casing assembly (500). When distal trocar portion (410) is coupled with anvil (320), anvil (320) also advances distally relative to tubular casing (512) of casing assembly (500), thereby increasing the distance between proximal surface (330) of the anvil (320) and distally presented deck surface of deck member (364), otherwise known as gap distance d. By rotating adjustment knob (460) in the opposite direction, monolithic closure rod (402) is actuated proximally relative to casing assembly (500) to reduce the gap distance d between anvil (320) and deck member (364) when distal trocar portion (410) is coupled with anvil (320). Thus, closure system (400) is operable to actuate monolithic closure rod (402) in response to rotating adjustment knob (460). Other configurations for closure system (400) will be apparent to one of ordinary skill in the art in view of the teachings herein.

Continuous groove (432) of the present example comprises a plurality of different portions (432A, 432B, 432C) that have a varying pitch or number of grooves per axial distance. The present groove (432) is divided into a distal portion (432A), a middle portion (432B) and a proximal portion (432C). Distal portion (432A) comprises a fine pitch or a high number of grooves over a short axial length of proximal grooved section (430). Middle portion (432B) comprises a section with comparably coarser pitch or fewer grooves per axial length such that relatively few rotations are required for the internal tab (462) of adjustment knob (460) to traverse along axial distance. When anvil (320) is in an initial, distal position in relation to tubular casing (512), the internal tab (462) of knob (460) is positioned in middle portion (432B). Accordingly, the gap distance d may be quickly reduced through relatively few rotations of adjustment knob (460) while the internal tab (462) traverses middle portion (432B). Proximal portion (432C) of the present example is substantially like distal portion (432A) and comprises a fine pitch or a high number of grooves over a short axial distance of proximal grooved section (430), such that a large number of rotations are required to traverse the short axial distance. Proximal portion (432C) of the present example is engaged by the internal proximal threading (466) defined by knob (460) when anvil (320) is substantially near deck member (364), such that indicator bar (456) moves within indicator window (506) along the set of indicia (not shown) to indicate that the anvil (320) gap distance d is within a desired operating range. Accordingly, when grooved proximal grooved section (430) reaches a proximal position where the proximal portion (432C) of groove (432) engages the internal proximal threading (466) of knob (460), each rotation of adjustment knob (460) may reduce the gap distance d by a relatively small amount to provide for fine tuning.

Connecting band portion (404) extends between proximal shank portion (420) and distal trocar portion (410) to connect a distal end of rod (422) and a proximal end of shaft (412). Connecting band portion (404) is sufficiently flexible to provide dynamic deformation of monolithic closure rod (402) along the longitudinal profile of preformed bent shaft portion (504) of casing assembly (500) as monolithic closure rod (402) translated relative to casing assembly (500).

Firing system (360) is substantially like firing system described above, with differences described below. Firing system (360) includes a trigger (370), a slidable trigger carriage (367), a driver actuator (365), a slidable staple driver member (362) defining a bore (366), a cylindraceous knife member (363), and a deck member (364); which are substantially like trigger (74), slidable trigger carriage (86), driver actuator (64), slidable staple driver member (250) defining bore (254), cylindraceous knife member (240), and deck member (220) described above, respectively, with differences described below.

Slidable staple driver member (362) includes a plurality of staple drivers (368), which are substantially like stapler drivers (252) described above. Deck member (364) houses a plurality of staples within staple pockets (not shown) that align with respective staple drivers (368). Staple drivers (368) are operable to drive staples from staple pockets of deck member (364), through an annular array of staple openings (not shown) of deck member (368), and against a plurality of staple forming pockets (332) of anvil (320), in accordance with the principles described above. Similar to cylindraceous knife member (240), cylindraceous knife member (363) is coupled with slidable staple driver member (362) in order to actuate with slidable staple driver member (362) to sever excess tissue radially interior to newly formed staples, in accordance with the principles described above.

Trigger (370) is pivotably coupled with casing assembly (500) and is configured to pivot relative to casing assembly (500) from an opened position to a closed position in order to actuate slidable staple driver member (362) and cylindraceous knife member (363) to staple and sever tissue captured between anvil (320) and deck member (364) during use, in accordance with the principles described above. Trigger (370) may be selectively fixed in the open position due to a lockout feature (371), which may be substantially like lockout feature (82) described above. Trigger (370) includes a handle (372). However, unlike trigger (74) having a separate spring (78) as described above, handle (372) includes an integral leaf spring (374) that is configured to bias trigger (370) toward the opened position relative to casing assembly (500). Handle (372) includes a pair of tabs (376), which may be like tabs (88) described above. Therefore, tabs (376) are configured to interact with slidable trigger carriage (367) when trigger (370) is pivoted to the closed position in order distally actuate trigger carriage (367), driver actuator (365), slidable staple driver member (362), and cylindraceous knife member (363). Like driver actuator (64) described above, driver actuator (365) comprises a tubular member having an open passageway such that adjacent portions of monolithic closure rod (402) may actuate longitudinally within and relative to driver actuator (365).

B. Exemplary Casing Assembly with Asymmetric Molded Shroud Components

Casing assembly (500) forms a mechanical ground for firing system (360) and closure system (400). As mentioned above, and as will be described in greater detail below, casing assembly (500) is configured to provide a consistently dimensioned mechanical ground for actuating components during exemplary use. Casing assembly (500) includes a first section (510) and a second section (560). First section (510) and second section (560) are asymmetrical pieces that are configured to couple with each other along a lateral dimension to house portions of firing system (360) and closure system (400).

First section (510) and second section (560) are each formed as unitary pieces and may be made through any suitable manufacturing process as would be apparent to one having ordinary skill in the art in view of the teachings herein, such as molding or 3D printing. When coupled together, first section (510) and second section (560) form a handle portion (502) and a preformed bent shaft portion (504). Therefore, first section (510) includes a corresponding handle portion (522) and a corresponding shaft portion (524); while second section (560) also includes a corresponding handle portion (562) and a corresponding shaft portion (564).

First section (510) and second section (560) each define a hollow interior (526, 566), respectively. When casing assembly (500) is properly assembled, hollow interiors (526, 566) cooperate to house and support portions of firing system (360) and closure system (400). Additionally, corresponding shaft portion (524) of first section (510) extends distally into a tubular casing (512) at a seamless connecting point (544); while corresponding shaft portion (564) of second section (560) extends distally into a semi-annular shoulder (580) and a semi-annular interior sleeve (582).

Tubular casing (512) is substantially like tubular casing (210) described above, with differences described below. Therefore, tubular casing (512) includes a cylindraceous inner core (520) substantially like cylindraceous inner core (212) of tubular casing (210). Tubular casing (512) angularly extends a full 360° about a longitudinal axis of tubular casing (512), without any seams. The interior of tubular casing (512) is in communication with hollow interiors (526, 566) such that distal trocar portion (410) may be slidably housed within inner core member (520), and such that driver actuation (365) may actuate slidable staple driver member (362) and cylindraceous knife member (363) housed within tubular casing (512). Unlike tubular casing (210) of instrument (10), tubular casing (512) is a unitary piece of first section (510) of casing assembly (500). In other words, tubular casing (512), handle portion (522), and corresponding shaft portion (524) together define a homogenous continuum of material. Therefore, tubular casing (512) is unitarily attached to both corresponding handle portion (522) and corresponding shaft portion (524) of first section (510). Because tubular casing (512) is unitarily formed with shaft portion (524) and handle portion (522) of first section (510), those pieces may not longitudinally compress or otherwise move longitudinally relative to each other in response to the high compressive forces associated with capturing tissue (2) between anvil (320) and deck member (364). This may prevent an undesirable tolerance stack during use of instrument (310).

Tubular casing (512) also includes a proximally presented semi-annular surface (542). Proximally presented semi-annular surface (542) is dimensioned to abut against semi-annular shoulder (580) when first section (510) and second section (560) are properly coupled to create a transition between corresponding shaft portion (564) and tubular casing (512). Therefore, when tubular casing (512) is under compression in respond to anvil (320) clamping tissue (2), some of the compressive forces will transfer to corresponding shaft portion (564) via the interaction between proximally presented semi-annular surface (542) and semi-annular shoulder (582). This may help prevent tubular casing (512) from bending relative to corresponding shaft portion (524) while being longitudinally compressed during use. Additionally, interior sleeve (580) is dimensioned for insertion into tubular casing (512). Interior sleeve (580) may abut against an interior surface of tubular casing (512) to help prevent lateral misalignment between corresponding shaft portions (522, 564) when properly coupled.

In the current example, proximally presented semi-annular surface (542) is associated with tubular casing (512) of first section (510). However, this is merely optional. Proximally presented semi-annular surface (542) may be associated with corresponding shaft portion (324). When shaft portion (324) of first section (510) includes proximally presented semi-annular surface (542), shaft portion (324) may completely form the segment of preformed bent shaft portion (504) distal to proximally presented semi-annular surface (542).

Each corresponding handle portion (522, 562) defines a portion of an indicator window (506), such that indicator window (506) is defined when first section (510) and second section (560) are coupled together. Like indicator window (120) described above, indicator window (506) has a set of indicia or some other kind of scale (now shown) and is dimensioned such that an operator may view indicator bar (456) against the indicia or scale to determine gap distanced. Additionally, when coupled together, first section (510) and second section (560) define a proximal opening (508), which rotatably supports adjustment knob (460) of closure system (400).

Figure 19:
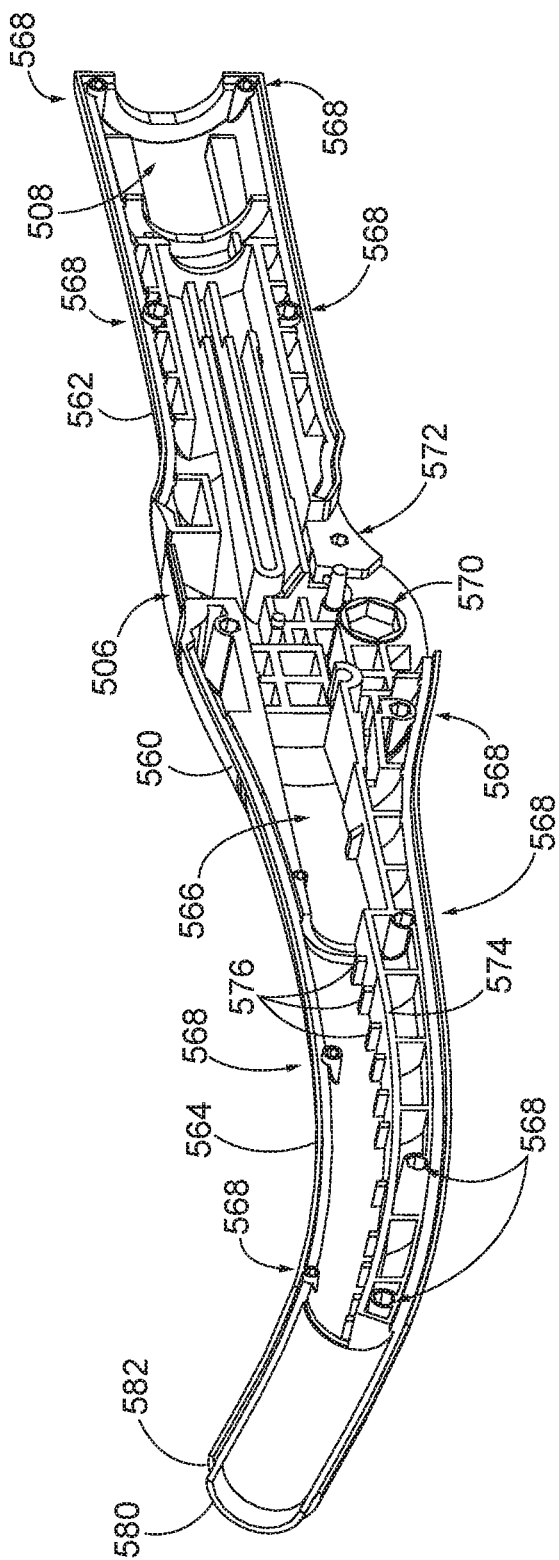
FIG. 19 depicts a perspective view of a first portion of the casing assembly of FIG. 16.
Figure 20:
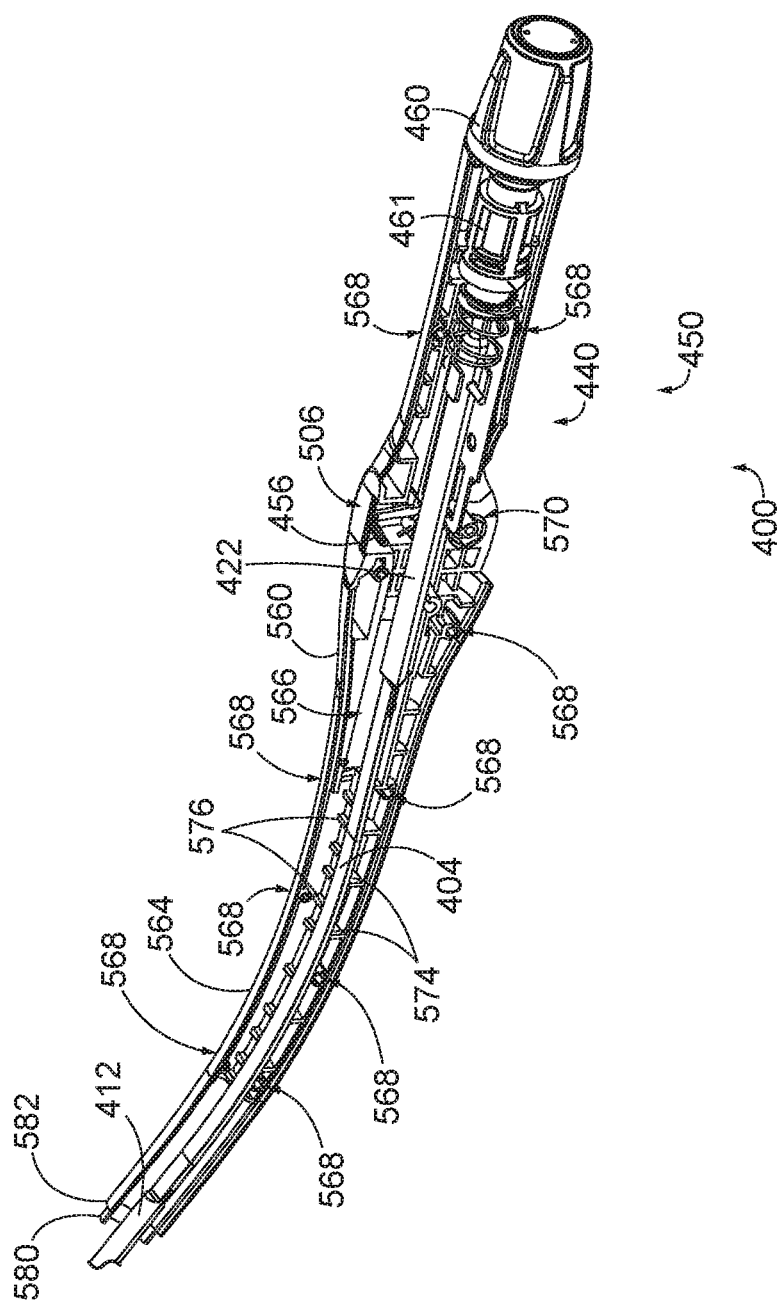
FIG. 20 depicts a perspective view of the first portion of FIG. 19 coupled with the closure system of FIG. 14.
Figure 21:
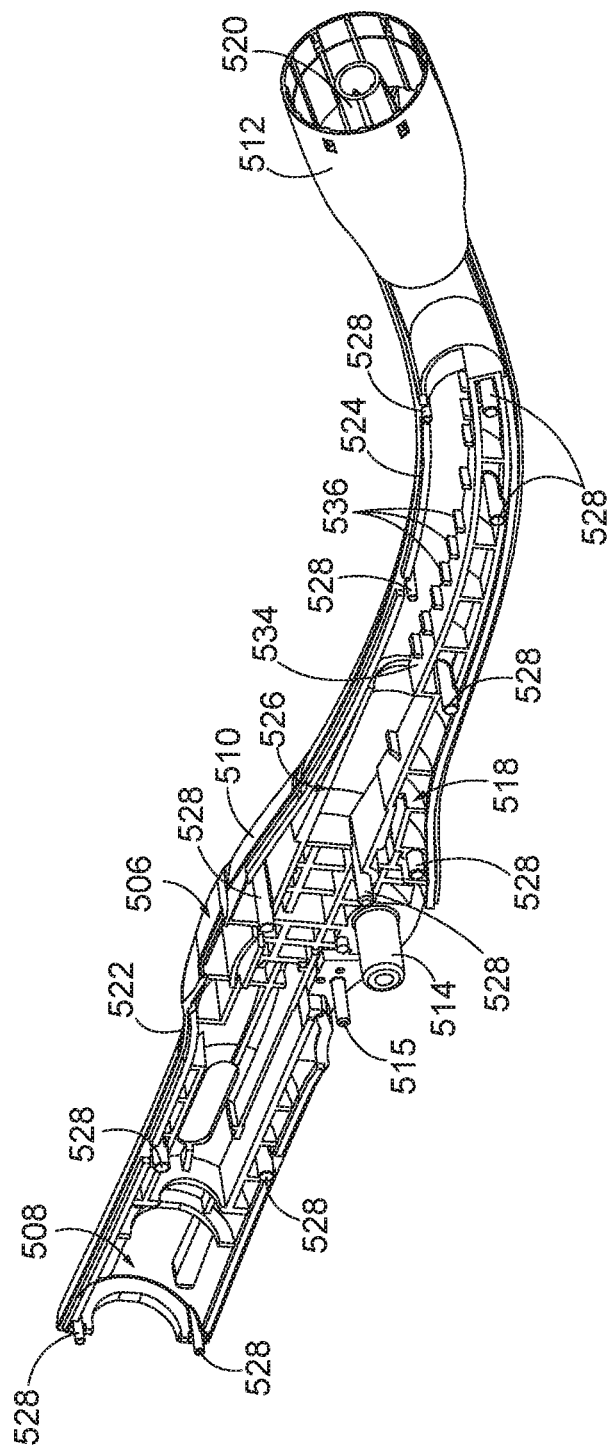
FIG. 21 depicts a perspective view of a second portion of the casing assembly of FIG. 16.
Figure 22:
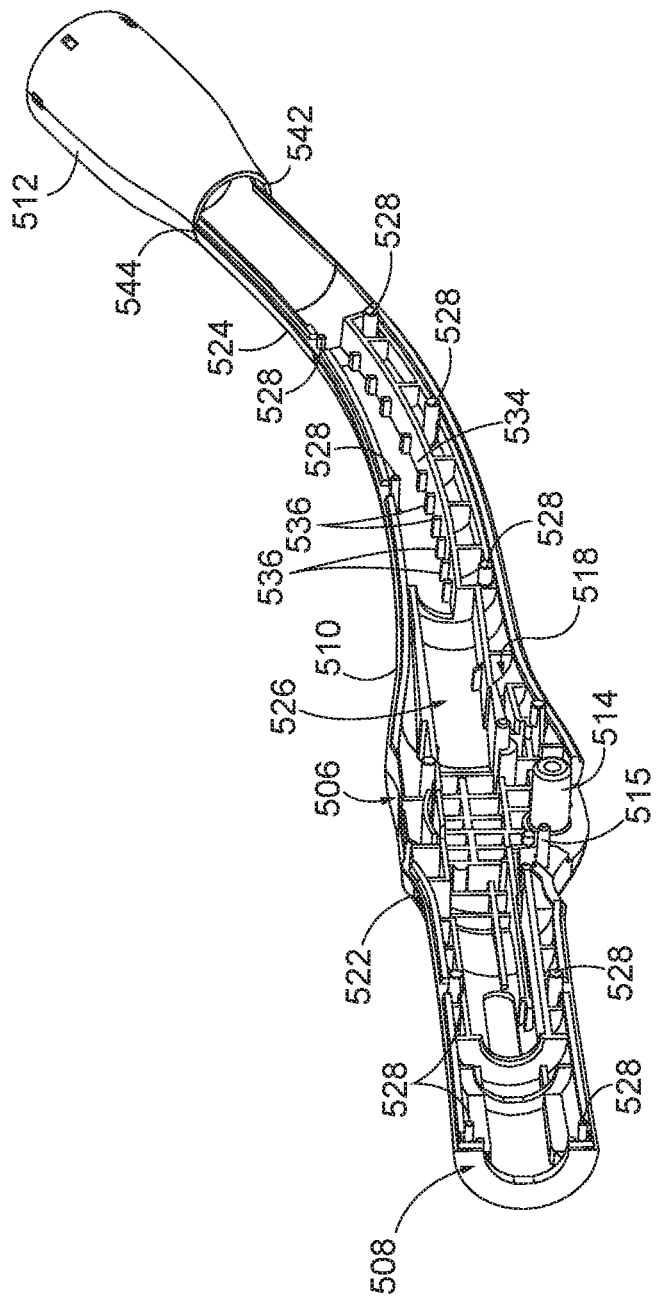
FIG. 22 depicts another perspective view of the second portion of FIG. 21.

As best seen in FIGS. 19-20, second section (560) defines a plurality of coupling bores (568), and a pair of pivot boss coupling bores (570, 572). As best seen in FIGS. 21-22, first section (510) includes a plurality of transversely extending locating rods (528), and a pair of transversely extending pivot bosses (514, 515). Transversely extending locating rods (528) are configured to be inserted within corresponding coupling bores (568) for a tight or interference fit such that first section (510) and second section (560) are coupled to each other. Therefore, transversely extending locating rods (528) and corresponding coupling bores (568) may couple first section (510) and second section (560) together to prevent longitudinal movement between first section (510) and second section (560), even under high compressive forces. This coupling may also prevent an undesirable tolerance stack during use.

Figure 23:
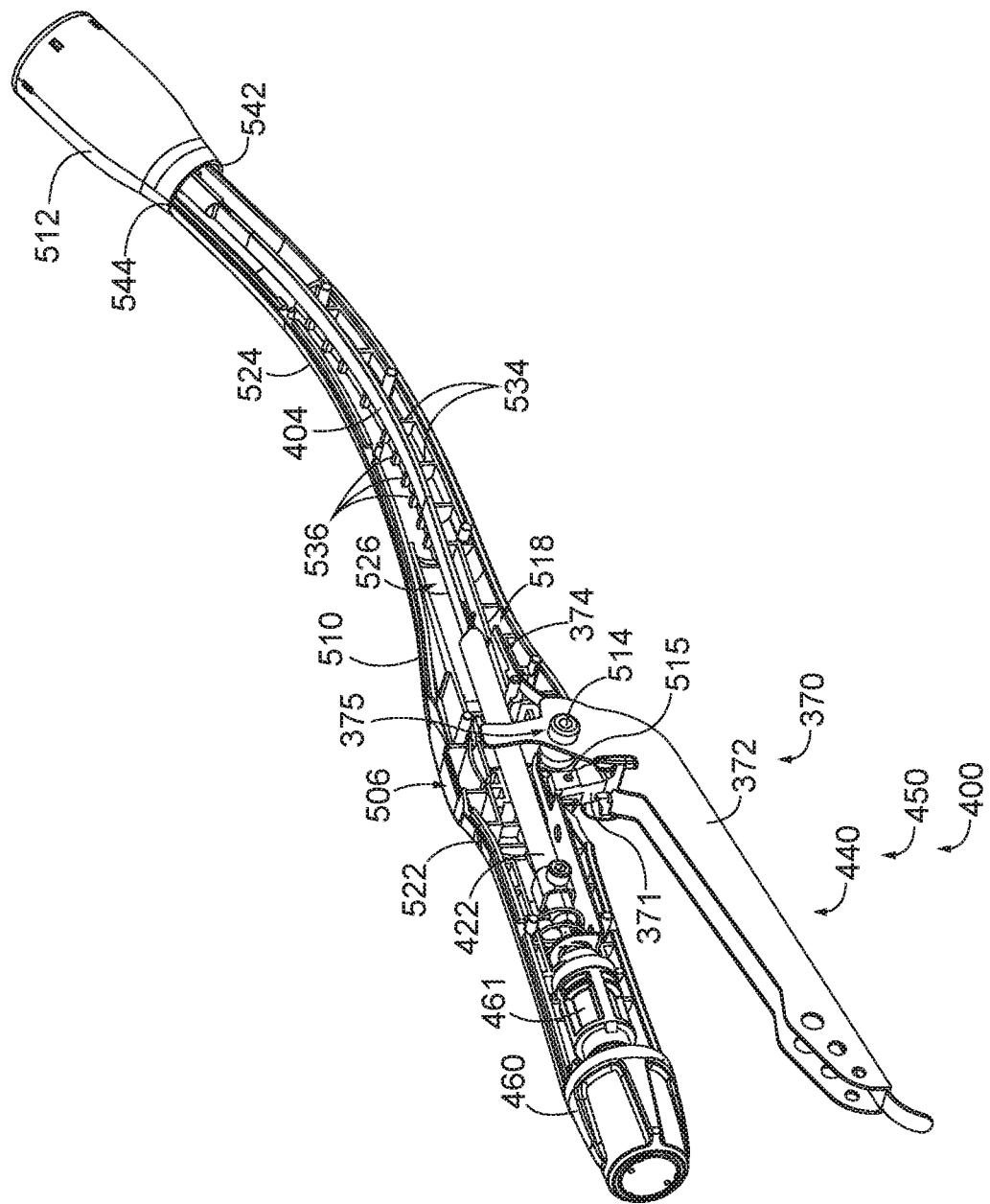
FIG. 23 depicts a perspective view of the second portion of FIG. 21 and the closure system of FIG. 14.
Figure 24:
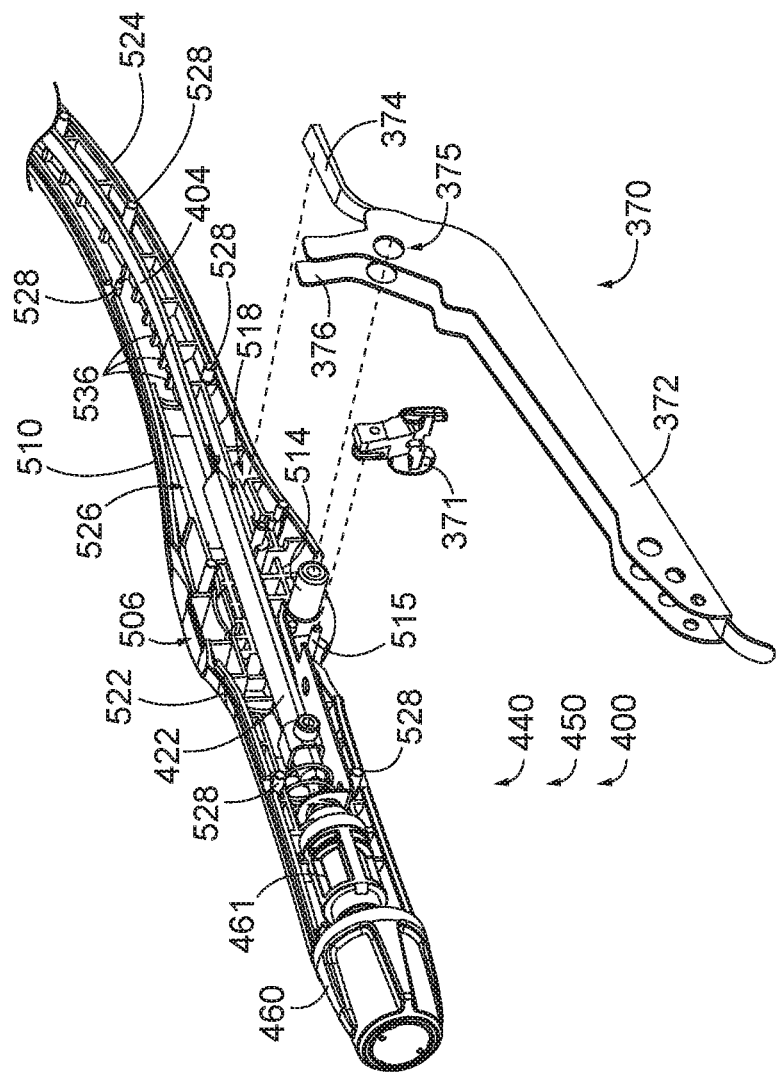
FIG. 24 depicts a partially exploded perspective view of the second portion of FIG. 21 and the closure system of FIG. 14.

Additionally, pivot boss coupling bores (570, 572) are configured to receive transversely extending pivot bosses (514, 515), respectively. As best seen in FIGS. 23-24, trigger (370) is rotatably mounted to casing assembly (500) via pivot boss (514) and pivot holes (375). Similarly, lockout feature (371) is rotatably mounted to casing assembly (500) via pivot boss (515). Therefore, when properly assembled, trigger (370) and lockout feature (371) may pivot relative to casing assembly (500) about pivot bosses (514, 515), respectively.

Figure 25:
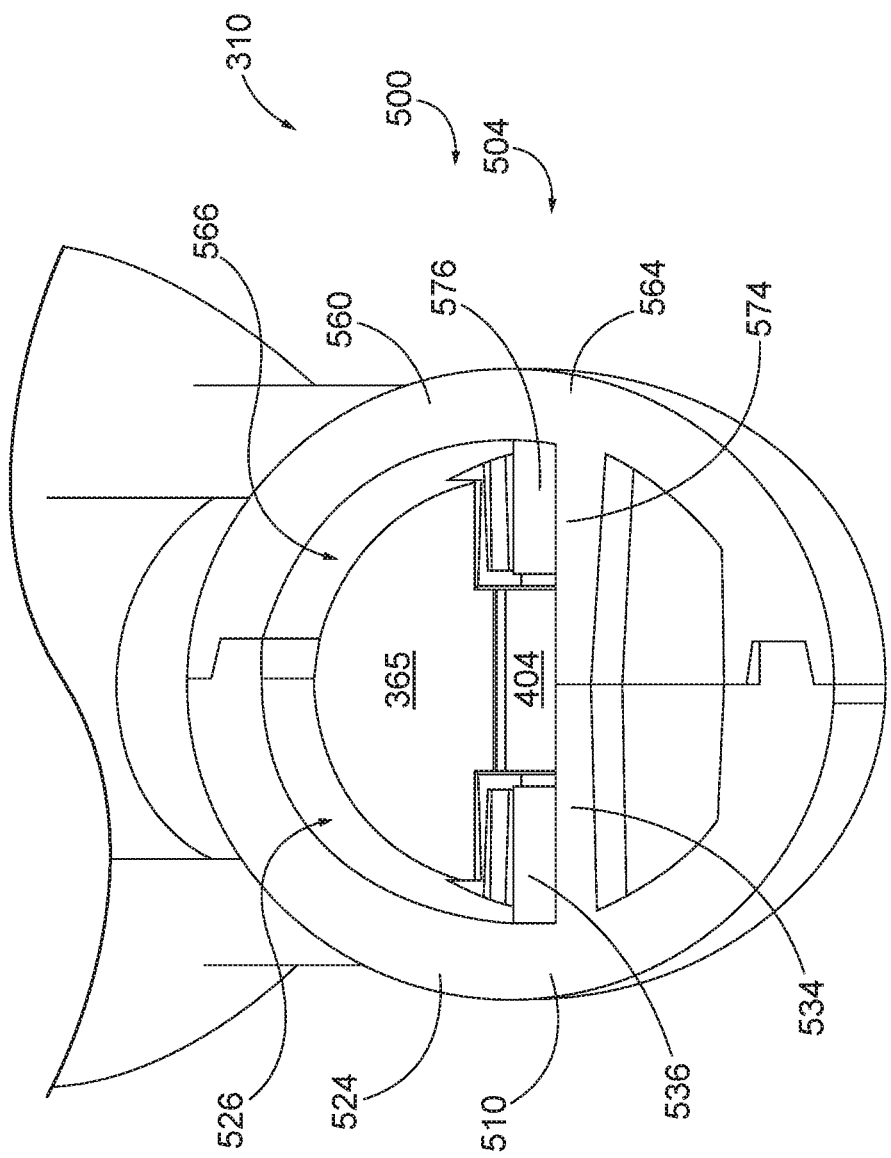
FIG. 25 depicts a cross-sectional view of the circular stapling surgical instrument of FIG. 12, taken along line 25-25 of FIG. 12.

Corresponding shaft portion (524) of first section (510) and corresponding shaft portion (564) of second section (560) each include an inwardly extending shelving rib (534, 574), respectively. As best seen in FIG. 25, shelving ribs (534, 574) are configured to come together when first section (510) and second section (560) are coupled, to provide a platform to slidably support band portion (404) of closure rod (402). Additionally, each shelving rib (534, 574) includes a longitudinal array of lateral alignment ribs (536, 576) extending upwardly from shelving ribs (534, 574), respectively. As also best seen in FIG. 25, lateral alignment ribs (536, 576) are dimensioned to laterally align band portion (404) of closure rod (402) relative to preformed bent shaft portion (504). In other words, lateral alignment ribs (536, 567) may abut against opposite lateral sides of band portion (404) to ensure that band portion (404) does not laterally deviate from its intended longitudinal path.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) an anvil defining an annular array of staple forming pockets; (b) a closure assembly comprising a trocar configured to selectively couple with the anvil and actuate the anvil between a distal position and a proximal position; (c) a firing assembly comprising: (i) a staple driver, and (ii) an annular array of staples, wherein the staple driver is operable to actuate between an unfired position and a fired position to drive the annular array of staples against the annular array of staple forming pockets when the anvil is in the proximal position; and (d) a casing assembly slidably housing at least a portion of the closure assembly and the firing assembly, wherein the casing assembly comprises: (i) a first section comprising: (A) first handle portion, (B) a first shaft portion extending distally from the handle portion, and (C) a tubular casing extending distally from the shaft portion, wherein the tubular casing slidably houses the staple driver, wherein the first section defines a homogenous continuum of material along the length of the first handle portion, the first shaft portion, and the tubular casing, and (ii) a second section comprising: (A) a second handle portion laterally coupled with the first handle portion, and (B) a second shaft portion extending distally from the second handle portion, wherein the second shaft portion is laterally coupled with the first shaft portion, wherein the second section defines a homogenous continuum of material along the length of the second handle portion and the second shaft portion.

Example 2

The apparatus of Example 1, wherein the closure assembly further comprises gap indicator assembly configured to determine a gap distance between the end effector and the anvil when the anvil is coupled to the trocar, wherein the gap indicator assembly comprises an indicator arm housed within the first handle portion and the second handle portion, wherein the first handle portion and the second handle portion cooperatively define an indicator window configured to display the indicator arm.

Example 3

The apparatus of any one or more of Examples 1 through 2, wherein the first shaft portion and the second shaft portion each define a preformed bent region.

Example 4

The apparatus of any one or more of Examples 1 through 3, wherein the closure system further comprises a band portion slidably housed within the preformed bent region.

Example 5

The apparatus of Example 4, wherein the first shaft portion comprises a first platform and a first plurality of lateral alignment ribs extending from the first platform, wherein the second shaft portion comprises a second platform and a second plurality of lateral alignment ribs extending from the second platform, wherein the first platform and the second platform are configured to slidably support the band portion, wherein the first plurality of alignment ribs and the second plurality of alignment ribs are dimensioned to laterally align the band portion within the casing assembly.

Example 6

The apparatus of any one or more of Examples 1 through 5, wherein the first section comprises a plurality of transversely extending alignment rods, wherein the second section comprises a plurality of coupling bores, wherein the first section and the second section are configured to couple with each other via the transversely extending alignment rods and the plurality of coupling bores.

Example 7

The apparatus of any one or more of Examples 1 through 6, wherein the firing assembly comprises a trigger, wherein the first section comprises a transversely extending pivot boss, wherein the trigger is pivotably coupled to the casing assembly via the transversely extending pivot boss.

Example 8

The apparatus of any one or more of Examples 1 through 7, wherein the closure assembly comprises a rotatable knob configured to actuate the trocar.

Example 9

The apparatus of Example 8, wherein the first section and the second section cooperatively define a proximal opening, wherein the rotatable knob is rotatably coupled to the casing assembly via the proximal opening.

Example 10

The apparatus of any one or more of Examples 1 through 9, wherein the firing assembly comprises a knife member coupled to the staple driver.

Example 11

The apparatus of any one or more of Examples 1 through 10, wherein the anvil comprises a proximally presented shank, wherein the trocar is configured to selectively couple with the anvil by a snap fitting with the proximally presented shank.

Example 12

The apparatus of any one or more of Examples 1 through 11, wherein the second shaft portion comprises an interior sleeve configured to fit within with tubular casing.

Example 13

The apparatus of Example 12, wherein the second shaft portion comprises a shoulder, wherein the tubular casing comprises a proximally presented surface, wherein the shoulder is configured to abut against the proximally presented surface when the first section and the second section are coupled.

Example 14

The apparatus of any one or more of Examples 1 through 13, wherein the tubular casing is connected with the first shaft portion at a seamless connecting point.

Example 15

An apparatus, comprising: (a) an anvil defining an annular array of staple forming pockets; (b) a closure assembly comprising a trocar and a band portion, wherein the trocar is configured to selectively couple with the anvil and actuate the anvil between a distal position and a proximal position; (c) a firing assembly comprising: (i) a staple driver, and (ii) an annular array of staples, wherein the staple driver is operable to actuate between an unfired position and a fired position to drive the annular array of staples against the annular array of staple forming pockets when the anvil is in the proximal position, and (d) a casing assembly slidably housing at least a portion of the closure assembly and the firing assembly, wherein the casing assembly comprises: (i) a first section comprising: (A) first handle portion, and (B) a first shaft portion extending distally from the handle portion, wherein the first shaft portion comprises a first shelving member and a first plurality of lateral alignment ribs extending from the first shelving member, wherein the first section defines a homogenous continuum of material extending along the length of the first handle portion and the first shaft portion, and (ii) a second section comprising: (A) a second handle portion, and (B) a second shaft portion extending distally from the second handle portion, wherein the second shaft portion comprises a second shelving member and a second plurality of lateral alignment ribs extending from the second shelving member, wherein the second section defines a homogenous continuum of material extending along the length of the second handle portion and the second shaft portion, wherein the first and second shelving members are configured to slidably support the band portion of the closing assembly, wherein the first and second plurality of lateral alignment ribs are configured to laterally align the band portion of the closing assembly relative to the casing assembly.

Example 16

The apparatus of Example 15, wherein the first and second shaft portions define a preformed bent portion.

Example 17

The apparatus of any one or more of Examples 15 through 16, wherein the band portion is unitarily connected to the trocar.

Example 18

The apparatus of any one or more of Examples 15 through 16, wherein the first section further includes a tubular casing that slidably houses the staple driver.

Example 19

The apparatus of Example 18, wherein the firing assembly further comprises a knife member fixed to the staple driver.

Example 20

An apparatus, comprising: (a) an anvil defining an annular array of staple forming pockets; (b) a closure assembly comprising a trocar configured to selectively couple with the anvil and actuate the anvil between a distal position and a proximal position; (c) a firing assembly comprising: (i) a staple driver, and (ii) an annular array of staples, wherein the staple driver is operable to actuate between an unfired position and a fired position to drive the annular array of staples against the annular array of staple forming pockets when the anvil is in the proximal position, and (d) a casing assembly slidably housing at least a portion of the closure assembly and the firing assembly, wherein the casing assembly comprises: (i) a first section comprising: (A) first handle portion, (B) a first shaft portion extending distally from the handle portion, and (C) a plurality of laterally extending male mating features, wherein the first handle portion, the first shaft portion, and the plurality of laterally extending male mating features together define a homogenous continuum of material, and (ii) a second section configured to couple with first section, wherein the second section comprises: (A) a second handle portion, (B) a second shaft portion extending distally from the second handle portion, and (C) a plurality of female mating features configured to receive the plurality of laterally extending male mating features to couple the first section with the second section, wherein the second handle portion, the second shaft portion, and the plurality of female mating features together define a homogenous continuum of material.

IV. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. patent application Ser. No. 13/693,430, entitled "Trans-Oral Circular Anvil Introduction System with Dilation Feature," filed Dec. 4, 2012, issued as U.S. Pat. No. 9,572,573 on Feb. 21, 2017, the disclosure of which is incorporated by reference herein; U.S. patent application Ser. No. 13/688,951, entitled "Surgical Staple with Integral Pledget for Tip Deflection," filed Nov. 29, 2012, issued as U.S. Pat. No. 9,289,207 on Mar. 22, 2016, the disclosure of which is incorporated by reference herein; U.S. patent application Ser. No. 13/706,827, entitled "Surgical Stapler with Varying Staple Widths along Different Circumferences," filed Dec. 6, 2012, now abandoned, the disclosure of which is incorporated by reference herein; U.S. patent application Ser. No. 13/688,992, entitled "Pivoting Anvil for Surgical Circular Stapler," filed Nov. 29, 2012, issued as U.S. Pat. No. 9,498,222 on Nov. 22, 2016, the disclosure of which is incorporated by reference herein; U.S. patent application Ser. No. 13/693,455, entitled "Circular Anvil Introduction System with Alignment Feature," filed Dec. 4, 2012, issued as U.S. Pat. No. 9,724,100 on Aug. 8, 2017, the disclosure of which is incorporated by reference herein; U.S. patent application Ser. No. 13/716,313, entitled "Circular Stapler with Selectable Motorized and Manual Control, Including a Control Ring," filed Dec. 17, 2012, issued as U.S. Pat. No. 9,532,783 on Jan. 3, 2017, the disclosure of which is incorporated by reference herein; U.S. patent application Ser. No. 13/716,318, entitled "Motor Driven Rotary Input Circular Stapler with Modular End Effector," filed Dec. 17, 2012, issued as U.S. Pat. No. 9,597,081 on Mar. 21, 2017, the disclosure of which is incorporated by reference herein; and/or U.S. patent application Ser. No. 13/716,323, entitled "Motor Driven Rotary Input Circular Stapler with Lockable Flexible Shaft," filed Dec. 17, 2012, issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an anvil defining an annular array of staple forming pockets;
   (b) a closure assembly comprising a coupling shaft and a band portion extending proximally relative to the coupling shaft, wherein the coupling shaft is configured to selectively couple with the anvil and actuate the anvil between a distal position and a proximal position;
   (c) a firing assembly comprising:
      (i) a staple driver, and
      (ii) an annular array of staples, wherein the staple driver is operable to actuate between an unfired position and a fired position to drive the annular array of staples against the annular array of staple forming pockets when the anvil is in the proximal position; and
   (d) a casing assembly slidably housing at least a portion of the closure assembly and the firing assembly, wherein the casing assembly comprises:
      (i) a first section comprising:
         (A) first handle portion,
         (B) a first shaft portion extending distally from the first handle portion, wherein the first shaft portion comprises a first preformed bend, a first platform extending along the first preformed bend, and a first longitudinal array of lateral alignment ribs extending from the first platform, and
         (C) a tubular casing extending distally from the first shaft portion, wherein the tubular casing slidably houses the staple driver,
         wherein the first section defines a homogenous continuum of material along a first length of the first handle portion, the first shaft portion, and the tubular casing, and
      (ii) a second section comprising:
         (A) a second handle portion laterally coupled with the first handle portion, and
         (B) a second shaft portion extending distally from the second handle portion, wherein the second shaft portion is laterally coupled with the first shaft portion such that the band portion of the closure assembly is slidably housed within the first shaft portion and the second shaft portion, wherein the second shaft portion comprises a second preformed bend, a second platform extending along the second preformed bend, and a second longitudinal array of lateral alignment ribs extending from the second platform,
         wherein the second section defines a homogenous continuum of material along a second length of the second handle portion and the second shaft portion,
         wherein the first platform and the second platform are configured to slidably support the band portion of the closure assembly, wherein the first longitudinal array of lateral alignment ribs and the second longitudinal array of lateral alignment ribs are dimensioned to laterally align the band portion of the closure assembly within the casing assembly through direct contact between the band portion, the first longitudinal array of lateral alignment ribs, and the second longitudinal array of lateral alignment ribs.

2. The apparatus of claim 1, wherein the closure assembly further comprises a gap indicator assembly configured to determine a gap distance between the tubular casing and the anvil when the anvil is coupled to the coupling shaft, wherein the gap indicator assembly comprises an indicator arm housed within the first handle portion and the second handle portion, wherein the first handle portion and the second handle portion cooperatively define an indicator window configured to display the indicator arm.

3. The apparatus of claim 1, wherein the first shaft portion and the second shaft portion each define a preformed bent region.

4. The apparatus of claim 1, wherein the first section comprises a plurality of transversely extending alignment rods, wherein the second section comprises a plurality of coupling bores, wherein the first section and the second section are configured to couple with each other via the transversely extending alignment rods and the plurality of coupling bores.

5. The apparatus of claim 1, wherein the firing assembly comprises a trigger, wherein the first section comprises a transversely extending pivot boss, wherein the trigger is pivotably coupled to the casing assembly via the transversely extending pivot boss.

6. The apparatus of claim 1, wherein the closure assembly comprises a rotatable knob configured to actuate the coupling shaft.

7. The apparatus of claim 6, wherein the first section and the second section cooperatively define a proximal opening, wherein the rotatable knob is rotatably coupled to the casing assembly via the proximal opening.

8. The apparatus of claim 1, wherein the firing assembly comprises a knife member coupled to the staple driver.

9. The apparatus of claim 1, wherein the anvil comprises a proximally presented shank, wherein the coupling shaft is configured to selectively couple with the anvil by a snap fitting with the proximally presented shank.

10. The apparatus of claim 1, wherein the second shaft portion comprises an interior sleeve configured to fit within the tubular casing.

11. The apparatus of claim 10, wherein the second shaft portion comprises a shoulder, wherein the tubular casing comprises a proximally presented surface, wherein the shoulder is configured to abut against the proximally presented surface when the first section and the second section are coupled.

12. The apparatus of claim 1, wherein the tubular casing is connected with the first shaft portion at a seamless connecting point.

13. An apparatus, comprising:
(a) an anvil defining an annular array of staple forming pockets;
(b) a closure assembly comprising a coupling shaft and a band portion extending proximally relative to the coupling shaft, wherein the coupling shaft is configured to selectively couple with the anvil and actuate the anvil between a distal position and a proximal position;
(c) a firing assembly comprising:
  (i) a staple driver, and
  (ii) an annular array of staples, wherein the staple driver is operable to actuate between an unfired position and a fired position to drive the annular array of staples against the annular array of staple forming pockets when the anvil is in the proximal position; and
(d) a casing assembly slidably housing at least a portion of the closure assembly and the firing assembly, wherein the casing assembly comprises:
  (i) a first section comprising:
    (A) first handle portion,
    (B) a first shaft portion extending distally from the first handle portion, wherein the first shaft portion defines a first preformed bend, wherein the first shaft portion comprises a first platform extending along the first preformed bend, and a first plurality of lateral alignment ribs extending from the first platform, and
    (C) a tubular casing extending distally from the first shaft portion, wherein the tubular casing slidably houses the staple driver,
    wherein the first section defines a homogenous continuum of material along a first length of the first handle portion, the first shaft portion, and the tubular casing, and
  (ii) a second section comprising:
    (A) a second handle portion laterally coupled with the first handle portion, and
    (B) a second shaft portion extending distally from the second handle portion, wherein the second shaft portion defines a second preformed bend, wherein the second shaft portion comprises a second platform extending along the second preformed bend, and a second plurality of lateral alignment ribs extending from the second platform, wherein the second shaft portion is laterally coupled with the first shaft portion,
    wherein the second section defines a homogenous continuum of material along a second length of the second handle portion and the second shaft portion, and
    wherein the first platform and the second platform are configured to directly contact the band portion to slidably support the band portion, wherein the first plurality of lateral alignment ribs and the second of lateral alignment ribs are configured to directly contact the band portion to thereby laterally align the band portion within the casing assembly.

14. An apparatus, comprising:
(a) an anvil defining an annular array of staple forming pockets;
(b) a closure assembly comprising a coupling shaft and a band portion extending proximally relative to the coupling shaft, wherein the coupling shaft is configured to selectively couple with the anvil and actuate the anvil between a distal position and a proximal position;
(c) a firing assembly comprising:
  (i) a staple driver, and
  (ii) an annular array of staples, wherein the staple driver is operable to actuate between an unfired position and a fired position to drive the annular array of staples against the annular array of staple forming pockets when the anvil is in the proximal position; and
(d) a casing assembly slidably housing at least a portion of the closure assembly and the firing assembly, wherein the casing assembly comprises:
  (i) a first section comprising:
    (A) first handle portion,
    (B) a first curved shaft portion extending distally from the first handle portion, wherein the first curved shaft portion comprises a first platform, and a first plurality of lateral alignment ribs extending from the first platform and
    (C) a tubular casing extending distally from the first curved shaft portion, wherein the tubular casing slidably houses the staple driver,
    wherein the first section defines a homogenous continuum of material along a first length of the first handle portion, the first curved shaft portion, and the tubular casing, and
  (ii) a second section comprising:
    (A) a second handle portion laterally coupled with the first handle portion, and
    (B) a second curved shaft portion extending distally from the second handle portion, wherein the second curved shaft portion is laterally coupled with the first curved shaft portion, wherein the second curved shaft portion comprises a second platform, and a second plurality of lateral alignment ribs extending from the second platform
    wherein the second section defines a homogenous continuum of material along a second length of the second handle portion and the second curved shaft portion, and
    wherein the first platform, the second platform, the first plurality of lateral alignment ribs, and the second plurality of lateral alignment ribs cooperatively define a recess slidably containing the band portion such that the first platform, the second platform, the first plurality of lateral alignment ribs, and the second plurality of lateral alignment ribs are in direct contact with the band portion.

* * * * *